US007935338B2

(12) United States Patent
Fanger et al.

(10) Patent No.: US 7,935,338 B2
(45) Date of Patent: May 3, 2011

(54) ANTIBODIES TO TREAT CANCER

(75) Inventors: Gary R. Fanger, Mill Creek, WA (US); Neil Fanger, Seattle, WA (US); David King, Belmont, CA (US); Marc W. Retter, Carnation, WA (US); Kenneth L. Rock, Chestnut Hill, MA (US)

(73) Assignees: University of Massachusetts, Boston, MA (US); Corixa Corporation, Hamilton, MT (US)

( * ) Notice: Subject to any disclaimer, the term of this patent is extended or adjusted under 35 U.S.C. 154(b) by 81 days.

(21) Appl. No.: 10/317,747

(22) Filed: Dec. 11, 2002

(65) Prior Publication Data

US 2004/0126378 A1  Jul. 1, 2004

Related U.S. Application Data

(60) Provisional application No. 60/339,736, filed on Dec. 11, 2001, provisional application No. 60/388,956, filed on Jun. 14, 2002, provisional application No. 60/399,103, filed on Jul. 26, 2002, provisional application No. 60/400,958, filed on Aug. 1, 2002.

(51) Int. Cl.
*A61K 39/395* (2006.01)
(52) U.S. Cl. .................... 424/130.1; 530/387.1
(58) Field of Classification Search .................. 435/329, 435/330; 424/130.1, 137.1, 138.1, 141.1, 424/133.1; 530/387.5, 387.7, 388.1, 387.1, 530/387.3, 388.8; 536/25.53
See application file for complete search history.

(56) References Cited

U.S. PATENT DOCUMENTS

| | | | |
|---|---|---|---|
| 4,965,198 A | | 10/1990 | Yamasaki et al. |
| 5,576,423 A | | 11/1996 | Aversa et al. |
| 5,688,657 A | | 11/1997 | Tsang et al. |
| 5,756,096 A | * | 5/1998 | Newman et al. ............ 424/154.1 |
| 5,817,513 A | * | 10/1998 | Lopez et al. .................. 435/329 |
| 5,830,470 A | * | 11/1998 | Nakamura et al. ......... 424/133.1 |
| 5,939,532 A | | 8/1999 | Nakamura et al. |
| 6,042,828 A | | 3/2000 | Nakamura et al. |
| 6,075,181 A | * | 6/2000 | Kucherlapati et al. .......... 800/25 |
| 6,180,370 B1 | * | 1/2001 | Queen et al. ................. 435/69.6 |
| 7,214,775 B2 | | 5/2007 | Hanai et al. |

FOREIGN PATENT DOCUMENTS

| | | |
|---|---|---|
| EP | 0369425 A1 | 5/1990 |
| EP | 0882794 A2 | 12/1998 |
| WO | WO-01/07481 A1 | 2/2001 |
| WO | WO 01/91793 A1 | 6/2001 |

OTHER PUBLICATIONS

Rudikoff et al (Proc Natl Acad Sci USA 1982 vol. 79 p. 1979), 1963.*
Hellstrom et al (Proc. Natl. Acad Sci USA, vol. 82, 1499-1502, Mar. 1985).*
Zhang et al (Int. J. Cancer. 1997, 73:42-49).*
Tai et al. (PNAS, vol. 80, pp. 5392-5396, 1983).*
Yamaguchi et al., "Human monoclonal antibody with dual GM2/GD2 specificity derived from an immunized melanoma patient", *Proc. Natl. Acad. Sci. USA*, 87:3333-3337 (May 1990).
Bergers, Gabriele et al., "Extrinsic regulators of epithelial tumor progression: metalloproteinases," *Current Opinion in Genetics & Development*, vol. 10:120-127 (2000).
Fernandes, Dancella M. et al., "A Monoclonal Antibody Reactive with a 40-kDa Molecule on Fetal Thymocytes and Tumor Cells Blocks Proliferation and Stimulates Aggregation and Apoptosis," *The Journal of Immunology*, vol. 163:1306-1314 (1999).
Kasai, Masataka et al., "A New Differentiation Antigen (FT-1) Shared with Fetal Thymocytes and Leukemia Cells in the Mouse," *J. Exp. Med.*, vol. 159:971-980 (1983).
Malard, Veronique et al., "21.1.1, A Novel Activation Marker of T and B Cells," *Molecular Immunology*, vol. 28(4/5):417-426 (1991).
Mountain, A. et al., "Engineering antibodies for therapy," *Biotechnol. Genet. Eng. Rev.*, vol. 10:1-142 (1992).
O'Boyle, Kevin P. et al.,"Patterns of Ganglioside Expression in B Cell Neoplasms," *Leukemia and Lymphoma*, vol. 21:255-266 (1996).
Pinto, Valerian B. et al., "Characterization of the Proliferative Response of a CD4-8-Thymic T Lymphoma Cell Line to Stimulation by Thymic Cellular Elements," *The Journal of Immunology*, vol. 147(1):42-49 (1991).
Reichert, Roger A. et al., "Ontogeny of Lymphocyte Homing Receptor Expression in the Mouse Thymus," *The Journal of Immunology*, vol. 136(10):3535-3542 (1986).
Retter, Marc W. et al., "Characterization of a Proapoptotic Antiganglioside GM2 Monoclonal Antibody and Evaluation of Its Therapeutic Effect on Melanoma and Small Cell Lung Carcinoma Xenografts," *Cancer Res.*, vol. 65:6425-6434 (2005).
Saito, Masaki et al., "Distinctive Characteristics of Ganglioside-Profiles in Human Leukemia-Lymphoma Cell Lines," *New Vistas in Glycolipid Research*, Ed. Akira Makita et al., Plenum Press, pp. 369-391 (1982).
Takashi, Tohru et al., "FT-2 Antigen for Distinguishing Lymphocyte Subpopulation in the Developing Thymus," *Immunology Letters*, vol. 9:259-262 (1985).
Takei, Fumio, "A New Differentiation Antigen of Proliferating Murine Thymocytes Identified by a Rat Monoclonal Antibody," *The Journal of Immunology*, vol. 132(2):766-771 (1984).
Tockman, Melvyn S. et al., "Considerations in Bringing a Cancer Biomarker to Clinical Application," *Cancer Research*, vol. 52:2711s-2718s (1992).
Warren, Andrew P. et al., "CD98: A Type II Transmembrane Glycoprotein Expressed from the Beginning of Primitive and Definitive Hematopoiesis May Play a Critical Role in the Development of Hematopoietic Cells," *Blood*, vol. 87(9):3676-3687 (1996).
Hanibuchi, M. et al. "Therapeutic efficacy of mouse-human chimeric anti-ganglioside GM2 monoclonal antibody against multiple organ micrometastases of human lung cancer in NK cell-depleted SCID mice," *Int. J. Cancer*, vol. 78:480-485 (1998).

(Continued)

*Primary Examiner* — Misook Yu
*Assistant Examiner* — Meera Natarajan
(74) *Attorney, Agent, or Firm* — Nelson Mullins Riley & Scarborough, LLP; Megan E. Williams

(57) ABSTRACT

Compositions and methods for the treatment of cancer, particularly melanoma, myeloma, small cell lung cancer, thymic lymphoma, T-cell lymphoma, B-cell lymphoma, osteosarcoma, and acute T-cell leukemia, are disclosed. Illustrative compositions include one or more anti-ganglioside antibodies and polynucleotides that encode such anti-ganglioside antibodies. These antibodies may be for example, hamster antibodies, chimeric human/hamster antibodies, or humanized antibodies. The disclosed compositions are useful, for example, in the treatment of cancer and can be used to induce apoptosis in a cancer cell.

50 Claims, 2 Drawing Sheets

OTHER PUBLICATIONS

Figure 1:
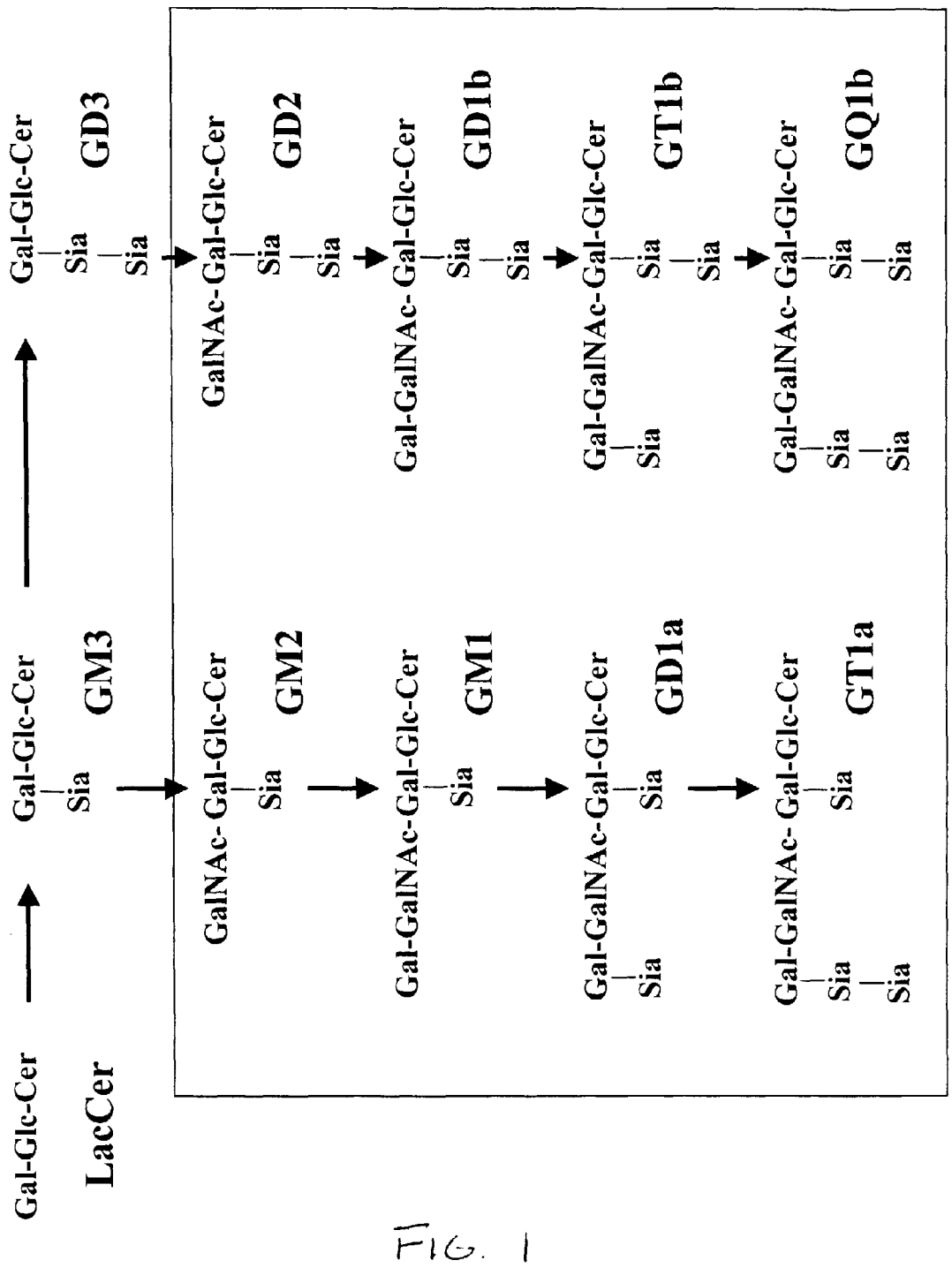

Irie, R.F., et al. "Human antibody to OFA-I, a tumor antigen, produced in vitro by Epstein-Barr virus-transformed human B-lymphoid cell lines," *Proc. Natl. Acad. Sci. USA*, vol. 79:5666-5670 (1982).

Magnani, John L. et al. "A Monosialoganglioside Is a Monoclonal Antibody-Defined Antigen of Colon Carcinoma," *Science*, vol. 212(3):55-56 (1981).

Vrionis, Fotios D. et al., "Five New Epitope-defined Monoclonal Antibodies Reactive with GM2 and Human Glioma and Medulloblastoma Cell Lines," *Cancer Research*, vol. 49:6645-6651 (1989).

Bernard, Alain et al., "A Unique Epitope on the CD2 Molecule Defined by the Monoclonal Antibody 9-1: Epitope-Specific Modulation of the E-Rosette Receptor and Effects on T-Cell Functions," *Human Immunology*, vol. 17:388-405 (1986).

Boyer, Cinda M. et al., "Relative Cytotoxic Activity of Immunotoxins Reactive with Different Epitopes on the Extracellular Domain of the c-*erb*B-2 (HER-2/*neu*) Gene Product p185," *Int. J. Cancer*, vol. 82:525-531 (1999).

Campbell, Peter et al., "Monoclonal antibody therapy for lymphoma," *Blood Reviews*, vol. 17:143-152 (2003).

De Santes, Kenneth et al., "Radiolabeled Antibody Targeting of the HER-2/*neu* Oncoprotein," *Cancer Research*, vol. 52:1916-1923 (1992).

Kim, Kwang-Mi et al., "Both the Epitope Specificity and Isotype are Important in the Antitumor Effect of Monoclonal Antibodies Against HER-2/*neu* Antigen," *Int. J. Cancer*, vol. 102:428-434 (2002).

Kipps, Thomas J. et al., "Importance of Immunoglobulin Isotype in Human Antibody-dependent, Cell-mediated Cytotoxicity Directed by Murine Monoclonal Antibodies," *J. Exp. Med.*, vol. 161:1-17 (1985).

Lewis, G.D. et al., "Differential responses of human tumor cell lines to anti-p185HER2 monoclonal antibodies," *Cancer Immunol. Immunother.*, vol. 37(4):255-263 (1993).

Masui, Hideo et al., "Mechanism of Antitumor Activity in Mice for Anti-Epidermal Growth Factor Receptor Monoclonal Antibodies with Different Isotypes," *Cancer Research*, vol. 46:5592-5598 (1986).

Pettersen, Rolf D. et al., "CD47 Signals T Cell Death," *The Journal of Immunotherapy*, vol. 162:7031-7040 (1999).

Press, Oliver W. et al., "Ricin A-chain Containing Immunotoxins Directed Against Different Isotopes on the CD2 Molecule Differ in Their Ability to Kill Normal and Malignant T Cells," *The Journal of Immunology*, vol. 141 (12):4410-4417 (1988).

Riemer, Angelika B. et al., "Matching of trastuzumab (Herceptin®) epitope mimics onto the surface of Her-2/neu—a new method of epitope definition," *Molecular Immunology*, vol. 42:1121-1124 (2005).

Vuist, Wim M.J. et al., "Two Distinct Mechanisms of Antitumor Activity Mediated by the Combination of Interleukin 2 and Monoclonal Antibodies," *Cancer Research*, vol. 50:5767-5772 (1990).

Casset, Florence et al., "A peptide mimetic of an anti-CD4 monoclonal antibody by rational design," *Biochemical and Biophysical Research Communications*, vol. 307:198-205 (2003).

Chen, Yvonne et al., "Selection and Analysis of an Optimized Anti-VEGF Antibody: Crystal Structure of an Affinity-matured Fab in Complex with Antigen," *J. Mol. Biol.*, vol. 293:865-881 (1999).

De Pascalis, Roberto et al., "Grafting of "Abbreviated" Complementarity-Determining Regions Containing Specificity-Determining Residues Essential for Ligand Contact to Engineer a Less Immunogenic Humanized Monoclonal Antibody," *The Journal of Immunology*, vol. 169:3076-3084 (2002).

Holm, Patrik et al., "Functional mapping and single chain construction of the anti-cytokeratin 8 monoclonal antibody TS1," *Molecular Immunology*, vol. 44:1075-1084 (2007).

MacCallum, Robert M. et al., "Antibody-antigen Interactions: Contact Analysis and Binding Site Topography," *J. Mol. Biol.*, Vol. 262:732-745 (1996).

Mueller, Barbara M. et al., "Expression of tissue factor by melanoma cells promotes efficient hematogenous metastasis," *Proc. Natl. Acad. Sci. USA*, vol. 89:11832-11836 (1992).

Vajdos, Felix F. et al., "Comprehensive Functional Maps of the Antigen-binding Site of an Anti-ErbB2 Antibody Obtained with Shotgun Scanning Mutagenesis," *J. Mol. Biol.*, vol. 320:415-428 (2002).

Wu, Herren et al., "Humanization of a Murine Monoclonal Antibody by Simultaneous Optimization of Framework and CDR Residues," *J. Mol.Biol.*, vol. 294:151-162 (1999).

Dillman, Robert O., "Monoclonal Antibody Therapy for Lymphoma," *Cancer Practice*, vol. 9(2):71-80 (2001).

Irie, Reiko F. et al., "Human Monoclonal Antibody to Ganglioside GM2 for Melanoma Treatment," The Lancet, vol. 1 (8641):786-787 (1989).

Miyake, Masayuki et al., "Generation of Two Murine Monoclonal Antibodies That Can Discriminate N-Glycolyl and N-Acetyl Neuraminic Acid Residues of GM2 Gangliosides," Cancer Research, vol. 48:6154-6160 (1988).

Nakamura, Kazuyasu et al., "Chimeric Anti-Ganglioside GM2 Antibody with Antitumor Activity," Cancer Research, vol. 54:1511-1516 (1994).

Natoli, Edward J. Jr. et al., "A Murine Monoclonal Antibody Detecting N-Acetyl- and N-Glycolyl-GM2: Characterization of Cell Surface Reaactivity," Cancer Research, vol. 46:4116-4120 (1986).

Nishinaka, Yumiko et al., "Development of a Human Monoclonal Antibody to Ganglioside GM2 with Potential for Cancer Treatment," Cancer Research, vol. 56:5666-5671 (1996).

Ohta, So et al., "Antitumor effects of a novel monoclonal antibody with high binding affinity to ganglioside GD3," Cancer Immunol. Immunother., vol. 36:260-266 (1993).

Ritter, Gerd et al., "Induction of Antibodies Reactive with GM2 Ganglioside After Immunization with Lipopolysaccharides from Campylobacter Jejuni," Int. J. Cancer, vol. 66:184-190 (1996).

\* cited by examiner

ANTIBODIES TO TREAT CANCER

REFERENCES TO RELATED APPLICATIONS

This application claims priority from the following U.S. Provisional Patent Applications: Ser. No. 60/339,736, filed on Dec. 11, 2001, Ser. No. 60/388,956, filed Jun. 14, 2002, Ser. No. 60/399,103, filed Jul. 26, 2002, and Ser. No. 60/400,958, filed Aug. 1, 2002. The contents of these provisional applications are incorporated herein by reference in their entireties.

FIELD OF THE INVENTION

The present invention relates to antibodies that can be used in the treatment of cancer, including myeloma, melanoma, and small cell lung cancer. It also relates to methods for the use of such antibodies that specifically bind to tumor cells, in which they can inhibit cellular proliferation, and induce apotosis.

BACKGROUND OF THE INVENTION

Gangliosides are glycosphingolipids that are present in high numbers on cells of neural crest origin as well as on a wide variety of tumor cells of neuroectodermal origin. Portoukalian et al., Eur. J. Biochem. 94:19-23 (1979); Yates et al., J. Lipid Res. 20:428-436 (1979). More specifically, expression of the gangliosides GD2, GD3, and GM2 has been reported in neuroblastoma, lung small cell carcinoma, and melanoma, each of which are highly malignant neuroectodermal tumors. J. Exp. Med., 155:1133 (1982); J. Biol. Chem. 257:12752 (1982); Cancer Res. 47:225 (1987); Cancer Res. 47:1098 (1987); Cancer Res. 45:2642 (1985); Proc. Natl. Acad. Sci. U.S.A. 80:5392 (1983).

The chemical structure of gangliosides includes a hydrophilic carbohydrate portion (one or more sialic acids linked to an oligosaccharide) attached to a hydrophobic lipid moiety composed of a long-chain base (sphingosine) and a fatty acid (ceramide). (G is an abbreviation for ganglioside and M, D, and T are abbreviations for mono, di, and tri, respectively; for further discussion of ganglioside nomenclature, see, Lehninger, Biochemistry, pp. 294-296 (Worth Publishers, 1981) and Wiegandt, in Glycolipids: New Comprehensive Biochemistry (Neuberger et al., ed., Elsevier, 1985), pp. 199-260; see, also, FIG. 1 for a schematic of ganglioside biosynthesis).

Gangliosides are believed to be involved in cell recognition, immunosuppression, adhesion and signal transduction. The ceramide portion anchors the ganglioside into the cell membrane and may, thereby, modulate intracellular signal transduction as a second messenger. The ganglioside designated GM2 is one of a group of sialic acid residue-containing glycolipids and is uniquely characterized by its presence in only trace amounts in normal cells and its upregulation in a variety of cancer cells such as, for example, lung small cell carcinoma, melanoma, and neuroblastoma.

Because they are immunogenic, gangliosides have received much attention as possible vaccine targets. For example, vaccination with a GM2 ganglioside, has been shown to stimulate high levels of anti-GM2 antibodies in melanoma patients. GM2 vaccines comprising either bacilli Calmette-Guerin (BCG) or, more recently, keyhole limpet hemagglutinin (KLH) as adjuvant have been tested in human clinical trials. Livingston et al., Proc. Natl. Acad. Sci U.S.A. 84:2911-2915 (1987); Livingston, In "Immunity to Cancer II." Eds MS Mitchell, Pub Alan L. Liss, Inc., NY; Irie et al. U.S. Pat. No. 4,557,931; Kirkwood et al. J. Clin. Oncol. 19(5):1430-1436 (2001); Chapman et al. Clin. Cancer Res. 6(3):874-879 (2000).

In an effort to develop a therapeutic agent against GM2-positive cells, a number of investigators have reported the production of anti-GM2 antibodies. For example, Yamaguchi et al., described the isolation of lymphocytes from a GM2-vaccinated patient and the transformation of those lymphocytes with Epstein-Barr virus to produce an antibody (designated 3-207) simultaneously reactive for both GM2 and GD2. Proc. Natl. Acad. Sci. USA 87:3333-3337 (1990). Similarly, Irie et al., disclosed a human monoclonal anti-GM2 antibody for melanoma treatment. Lancet 1:786-787 (1989); see, also, Tai et al., Proc. Nat. Acad. Sci. U.S.A. 80:5392-5396 (1983) (disclosing a human anti-GM2 monoclonal antibody designated L55) and Yamasaki et al. U.S. Pat. No. 4,965,498 (disclosing a monoclonal antibody specific to a sugar chain containing an N-glycolylneuramine acid and having the ability to bind to at least N-glycolyl GM2 ganglioside). Furthermore, Ritter et al., disclosed antibodies produced following immunization with a lipopolysaccharide antigen of Campylobacter jejuni that reportedly binds to monosialogangliosides, including both GM2 and GM1. Int. J. Cancer 66(2):184-190 (1996).

Nakamura et al. have described two murine anti-GM2 monoclonal IgM antibodies, KM696 and KM697, as well as corresponding chimeric antibodies, KM966 and KM967, constructed by replacing the variable domain heavy and light chain cDNAs of a human IgG1 with the corresponding variable domain heavy and light chain cDNAs of KM696 and KM697, respectively. Cancer Research 54:1511-1516 (1994); U.S. Pat. Nos. 5,830,470 and 5,874,255. These investigators also reported CDR-grafted variants of the KM696/KM966 and the KM697/KM967 antibodies designated KM8966 and KM8967, respectively. U.S. Pat. Nos. 5,939,532 and 6,042,828. Indirect immunofluorescence staining of tumor cell lines with the KM966 chimeric antibody demonstrated that GM2 was expressed on pulmonary tumor cells and leukemia cells as well as neuroectodermal origin tumor cells.

SUMMARY OF THE INVENTION

The invention is based on the discovery that certain antibodies, e.g., monoclonal antibodies, specifically bind to monosialo-GM2 on the surface of numerous types of tumor cells, but do not bind to other gangliosides. These monoclonal antibodies can block proliferation and induce apoptosis of tumor cells to which they specifically bind.

The invention features a method of inhibiting proliferation of a myeloma tumor cell expressing a ganglioside antigen (e.g., monosialo-GM2, asialo-GM2, disialo-GM2, monosialo-GM3, disialo-GD1a, disialo-GD1b, asialo-GM1, monosialo-GM1, lysosialo-GM1, trisialo-GT1b, and disialo-GD3) in which the method includes contacting the cell with an antibody (e.g., chimeric antibody, a humanized antibody, a human antibody, a primatized antibody, DMF10.167.4, DMF10.62.3, a chimeric antibody having a variable region of DMF10.167.4, a chimeric antibody having a variable region of DMF10.62.3, a humanized antibody having all complementary determinant regions of DMF 10.67.4, and a chimeric antibody with a light chain amino acid sequence of SEQ ID NO:21 (e.g., isoleucine at linear position 52 is replaced with valine), in which a heavy chain amino acid sequence of SEQ ID NO:22 (e.g., threonine at linear position 78 of SEQ ID NO:22 is replaced with lysine), and the antibody specifically binds to the ganglioside.

The invention also features a method of inhibiting the proliferation of a cancer cell (e.g., a thymic lymphoma, T-cell lymphoma, B-cell lymphoma, melanoma, osteosarcoma, acute T-cell leukemia, small cell lung cancer, and myeloma cell) in which the method includes contacting the cell with a chimeric antibody (e.g., administered in vivo to a mammal,) that includes a light chain amino acid sequence of SEQ ID NO:21 (e.g., in which isoleucine at linear position 52 is replaced with valine) and a heavy chain amino acid sequence of SEQ ID NO:22 (e.g., in which threonine at linear position 78 is replaced with lysine).

The invention further features a purified chimeric antibody (e.g., an antibody that is effective in inhibiting cell proliferation of a tumor cell to which the antibody specifically binds, an antibody that is effective in inducing apoptosis in a tumor cell to which the antibody specifically binds, an antibody that binds specifically to monosialo-GM2 on the surface of a tumor cell and induces apoptosis in a monolayer, a single-cell suspension of the tumor cells, or both, an antibody that includes a light chain having the amino acid sequence of SEQ ID NO:21 and a heavy chain having the amino acid sequence of SEQ ID NO:22, or an antibody that binds specifically to monosialo-GM2 on the surface of a tumor cell and induces apoptosis in a monolayer, a single-cell suspension of tumor cells, or both), or antigen-binding fragment thereof, in which the chimeric antibody includes an amino acid sequence comprising SEQ ID NO:21 (e.g., in which isoleucine at linear position 52 is replaced with valine) or SEQ ID NO:22 (e.g., in which threonine at linear position 78 is replaced with lysine).

The invention includes an purified antibody light chain that includes the sequence of SEQ ID NO:21.

Additionally, the invention includes an isolated nucleic acid molecule that includes a nucleotide sequence (e.g., the nucleotide sequence comprises SEQ ID NO:8) including that encodes the antibody light chain of a purified antibody light chain (e.g., in which isoleucine at linear position 52 of the light chain consisting of SEQ ID NO:21 is replaced with valine) that includes the sequence of SEQ ID NO:21.

The invention further includes an isolated nucleic acid molecule that includes a nucleotide sequence that encodes the antibody light chain in which isoleucine at linear position 52 of SEQ ID NO:21 is replaced with valine.

The invention also includes a purified antibody that includes the light chain of claim that includes the sequence of SEQ ID NO:21 and a heavy chain.

Also featured in the invention is a purified antibody heavy chain having the amino acid sequence of SEQ ID NO:22 (e.g., wherein a threonine at linear position 78 is replaced with a lysine).

The invention further features an isolated nucleic acid molecule in which the nucleic acid molecule includes a nucleic acid sequence that encodes the antibody heavy chain having the amino acid sequence of SEQ ID NO:22 (e.g., wherein a threonine at linear position 78 is replaced with a lysine).

Also featured as part of the invention is an isolated nucleic acid molecule in which the nucleic acid molecule (e.g., including the nucleic acid sequence of SEQ ID NO:7) encodes the antibody heavy chain of the amino acid sequence of SEQ ID NO:22.

The invention also includes a purified antibody comprising the heavy chain having the amino acid sequence of SEQ ID NO:22.

The invention additionally features a purified antibody (e.g., an antibody effective in inhibiting cell proliferation of a tumor cell to which the antibody specifically binds, an antibody effective in inducing apoptosis in a tumor cell to which the antibody specifically binds, or an antibody that binds specifically to monosialo-GM2 on the surface of a tumor cell and induces apoptosis in a monolayer, a single-cell suspension of the tumor cells, or both), or antigen-binding fragment thereof, wherein the antibody comprises a complementary determinant region (CDR) with an amino acid sequence of SEQ ID NO: 13, SEQ ID NO: 14, SEQ ID NO:15, SEQ ID NO:16, SEQ ID NO:17, or SEQ ID NO:18.

The invention also includes a method of inhibiting growth of a tumor cell (e.g., in which growth of the tumor cell is inhibited by inhibiting proliferation of the cell, in which the growth of the tumor cell is inhibited by inducing apoptosis of the cell) in which the method includes contacting the tumor cell with a chimeric antibody having a light chain amino acid sequence of SEQ ID NO:21 and a heavy chain amino acid sequence of SEQ ID NO:22.

The invention further includes an isolated nucleic acid that includes the nucleic acid sequence of SEQ ID NO:5, 6, 9, 10, 11, or 12.

Additionally, the invention includes a polypeptide that includes the amino acid sequence of SEQ ID NO:19, 20, 23, 24, 25, or 26.

The invention also includes a purified monoclonal antibody, or antigen-binding fragment thereof, in which the monoclonal antibody comprises an amino acid sequence of SEQ ID NO: 19, 20, 23, 24, 25, or 26.

The invention further features an antibody, or antigen-binding fragment thereof, in which the antibody comprises a complementary determinant region (CDR) with an amino acid sequence of SEQ ID NO:13, SEQ ID NO:14, SEQ ID NO:15, SEQ ID NO:16, SEQ ID NO:17, or SEQ ID NO:18.

As used in this specification and the appended claims, the singular forms "a," "an" and "the" include plural references unless the content clearly dictates otherwise.

An "isolated nucleic acid sequence" is a nucleic acid sequence that is substantially free of the genes that flank the nucleic acid sequence in the genome of the organism in which it naturally occurs. The term therefore includes a recombinant nucleic acid sequence incorporated into a vector, into an autonomously replicating plasmid or virus, or into the genomic nucleic acid sequence of a prokaryote or eukaryote. It also includes a separate molecule such as a cDNA, a genomic fragment, a fragment produced by polymerase chain reaction (PCR), or a restriction fragment.

An antibody that "specifically binds" to monosialo-GM2 binds to monosialo-GM2, but that does not recognize and bind to other molecules in a sample, such as a biological sample that naturally includes monosialo-GM2.

"Conservative" amino acid substitutions are substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Any one of a family of amino acids can be used to replace any other members of the family in a conservative substitution.

The terms "polypeptide, peptide, and protein" are used interchangeably herein to refer to a chain of amino acid residues.

An "antigen-binding fragment" of an antibody is a portion of the antibody that is capable of binding to an epitope on an antigen (for example, monosialo-GM2) bound by the full antibody.

An "epitope" is a particular region of an antigen (for example, monosialo-GM2) to which an antibody binds and which is capable of eliciting an immune response.

An "isolated" antibody is an antibody that is substantially free from other naturally-occurring organic molecules with which it is naturally associated.

An antibody or other molecule that blocks cell proliferation is an antibody or molecule that inhibits cell cycle, division, or both.

A "reporter group" is a molecule or compound that has a physical or chemical characteristic such as luminescence, fluorescence, enzymatic activity, electron density, or radioactivity that can be readily measured or detected by appropriate detector systems or procedures.

"Contacting" a cell with an antibody includes both in vivo and in vitro methods whereby an antibody may specifically bind to an antigen. The antigen can be expressed on the surface of a cell. Such methods include for example administering a solution containing the antibody (e.g. through an injection or other methods known in the art) to a mammal. Additionally, in vitro methods of contacting a cell with an antibody include adding the antibody to a solution or cell culture dish in which the test cells are growing.

An antibody may inhibit the proliferation of a cell though mechanisms including, but not limited to, inducing apoptosis, mediating antibody dependent cellular cytotoxicity, mediating complement dependent cytotoxicity, blocking angeogensis or destroying vasculature.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained more fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention features antibodies that recognize monosialo-GM2 expressed on tumor cells. The antibodies can be used to inhibit proliferation of tumor cells and induce apoptosis of tumor cells to which they specifically bind. The monoclonal antibodies can be used diagnostically (for example, to determine the presence of malignant cells), or can be used therapeutically to treat tumor cells by themselves or through their delivery of an attached antitumor agent.

Other features and advantages of the invention will be apparent from the following detailed description, and from the claims.

BRIEF DESCRIPTION OF THE DRAWINGS AND SEQUENCE LISTING

FIG. 1 is a diagrammatic representation of ganglioside biosynthesis. It employs the following abbreviations: Cer, ceramide; Glc, glucose; Gal, galactose; GalNAc, N-acetylgalactosamine; Sia, sialic acid; LacCer, lactosylceramide. This figure is adapted from Takamiya et al., Proc. Natl. Acad. Sci. USA 93:10662 (1996).

Figure 2:
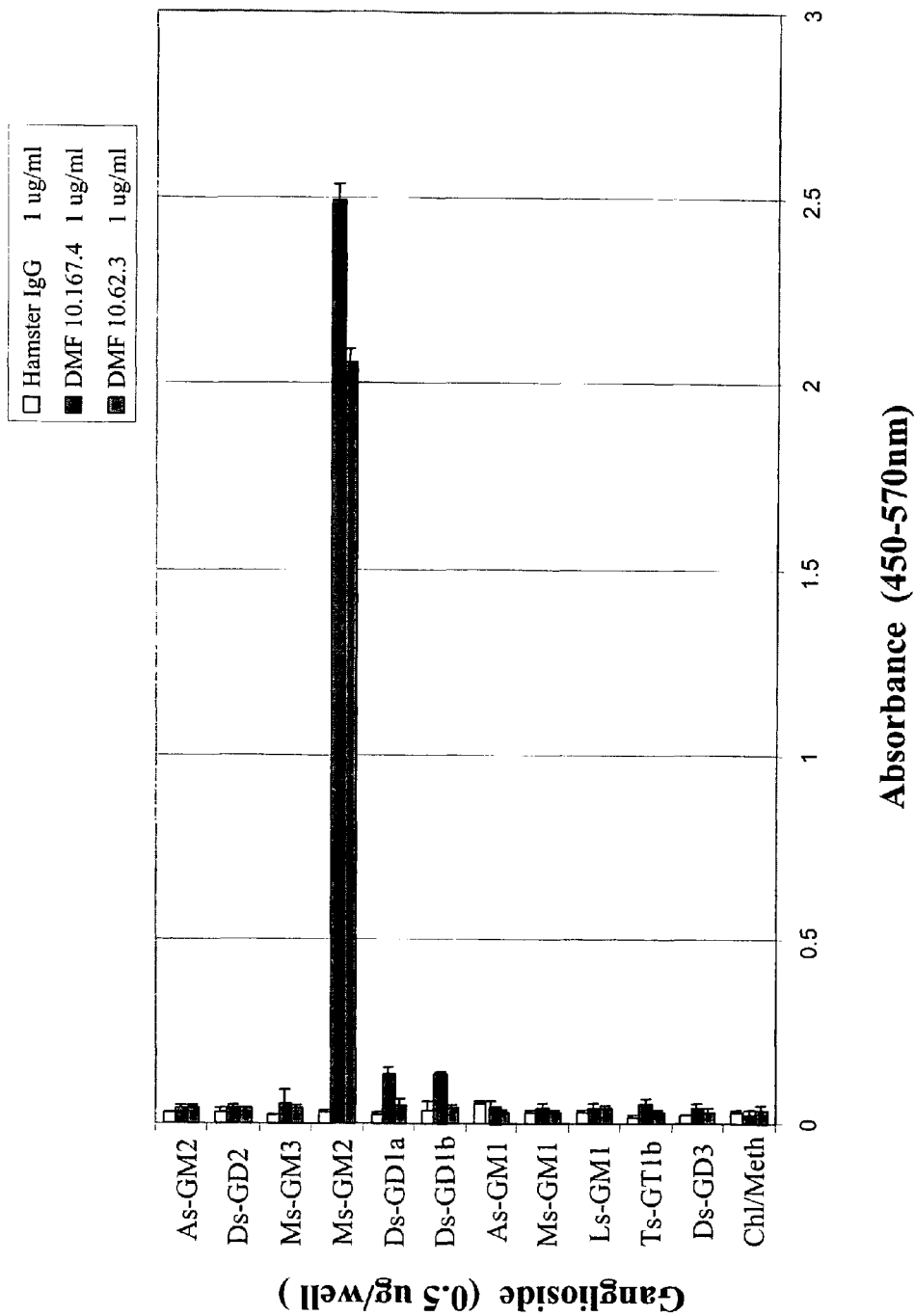

FIG. 2 is a bar graph depicting the ganglioside binding activity of the hamster monoclonal antibodies designated DMF 10.167.4 and DMF 10.62.3. It employs the following abbreviations: As=asialo, Ms=monosialo, Ds=disialo, Ts=trisialo, and Ls=lysosialo and Chl/Meth=Chloroform Methanol diluent.

SEQ ID NO: 1 is the polynucleotide sequence of an antisense primer for the light chain of a chimeric anti-monosialo-GM2 antibody.

SEQ ID NO: 2 is the polynucleotide sequence of a sense primer for the light chain of a chimeric anti-monosialo-GM2 antibody.

SEQ ID NO: 3 is the polynucleotide sequence of an antisense primer for the heavy chain of a chimeric anti-monosialo-GM2 antibody.

SEQ ID NO: 4 is the polynucleotide sequence of a sense primer for the heavy chain of a chimeric anti-monosialo-GM2 antibody.

SEQ ID NO: 5 is the polynucleotide sequence of the VJ of DMF10.62.3.

SEQ ID NO: 6 is the polynucleotide sequence of the VDJ of DMF10.62.3.

SEQ ID NO: 7 is the polynucleotide sequence the VJ-C (light chain) of a chimeric anti-monosialo-GM2 antibody.

SEQ ID NO: 8 is the polynucleotide sequence of the VDJ-C (heavy chain) of a chimeric anti-monosialo-GM2 antibody.

SEQ ID NO: 9 is the polynucleotide sequence of the VJ of DMF10.167.4.

SEQ ID NO: 10 is the polynucleotide sequence of the VDJ of DMF10.167.4.

SEQ ID NO: 11 is the polynucleotide sequence of the VJ of DMF10.167.4 with its endogenous leader sequence.

SEQ ID NO: 12 is the polynucleotide sequence of the VDJ of DMF10.167.4 with its endogenous leader sequence.

SEQ ID NO: 13 is the amino acid sequence of CDR3 of the light chain of DMF10.167.4 and DMF10.62.3.

SEQ ID NO: 14 is the amino acid sequence of CDR2 of the light chain of DMF10.167.4 and DMF10.62.3.

SEQ ID NO: 15 is the amino acid sequence of CDR1 of the light chain of DMF10.167.4 and DMF10.62.3.

SEQ ID NO: 16 is the amino acid sequence of CDR3 of the heavy chain of DMF10.167.4 and DMF10.62.3.

SEQ ID NO: 17 is the amino acid sequence of CDR2 of the heavy chain of DMF10.167.4 and DMF10.62.3.

SEQ ID NO: 18 is the amino acid sequence of CDR1 of the heavy chain of DMF10.167.4 and DMF10.62.3.

SEQ ID NO: 19 is the amino acid sequence of the VJ of DMF10.62.3.

SEQ ID NO: 20 is the amino acid sequence of the VDJ of DMF10.62.3.

SEQ ID NO: 21 is the amino acid sequence of the VJ-C (light chain) of a chimeric anti-monosialo-GM2 antibody.

SEQ ID NO: 22 is the amino acid sequence of the VDJ-C (heavy chain) of a chimeric anti-monosialo-GM2 antibody.

SEQ ID NO: 23 is the amino acid sequence of the VJ of DMF10.167.4.

SEQ ID NO: 24 is the amino acid sequence the VDJ of DMF10.167.4.

SEQ ID NO: 25 is the amino acid sequence of the VJ of DMF10.167.4 with its endogenous leader sequence.

SEQ ID NO: 26 is the amino acid sequence of the VDJ of DMF10.167.4 with its endogenous leader sequence.

DETAILED DESCRIPTION

The present invention features antibodies, e.g., monoclonal antibodies that specifically bind to monosialo-GM2. Monosialo-GM2 occurs on a variety of types of tumor cells, including thymic lymphoma, T-cell tumor, a B-cell lymphoma, melanoma, osteosarcoma, and acute T-cell leukemia. Importantly, it was demonstrated that monosialo-GM2 is over-expressed on certain myeloma cell lines. Expression of monosialo-GM2 has also been observed in a variety of different species, including humans, monkeys, and mice. Upon binding of an antibody of the invention to a cell over-expressing monosialo-GM2, the cell stops proliferating and undergoes apoptosis. The antibodies of the invention (e.g., DMF 10.167.4 and ChGM2) can be used to treat myeloma. They can be used to treat melanoma and small cell lung carcinoma. Additionally, they can be used to treat other cancers, e.g., hematological malignancies, breast cancers, ovarian cancers, uterine cancers, lung cancers, GI cancers (including those affecting the oropharynx, esophagus, stomach, small and large intestine, rectum), pancreatic cancer, liver cancer, biliary cancers, kidney cancer, skin cancers, adrenal cancers, endocrine cancers, brain cancers, neural cancers, bladder cancer, bone cancer, connective tissue cancers, squamous cell carcinoma, adenocarcinoma, and mesothelioma, provided that the cancer expresses or over-expresses monosialo-GM2.

Three hybridoma cell lines that produce monoclonal antibodies that specifically bind to monosialo-GM2 have been deposited with the ATCC under Accession No. PTA-377 (DMF10.62.3), Accession No. PTA-405 (DMF10.167.4), or Accession No. PTA-404 (DMF10.34.36).

The antibodies described herein have a variety of uses. The antibodies can be used in in vitro diagnostic assays to determine the presence of malignant cells in mammalian, e.g., human, tissues. The antibodies can also be used to localize and image tumors in vivo by administering to a subject an isolated antibody described herein which is labeled with a reporter group. The antibodies also have therapeutic applications, such as to treat tumors or deliver an anti-tumor agent (e.g., as a treatment for myeloma, small cell lung carcinoma, or melanoma).

Methods of Making Antibodies

Antibodies are immunoglobulin molecules and immunologically active portions of immunoglobulin molecules. Examples of fragments of immunoglobulin molecules include fragments of an antibody, e.g., F(ab) and F(ab')$_2$ portions, which can specifically bind to monosialo-GM2. Fragments can be generated by treating the antibody with an enzyme such as pepsin. The term monoclonal antibody or monoclonal antibody composition refers to a population of antibody molecules that contain only one species of an antigen binding site capable of immunoreacting with a particular epitope of, e.g., a ganglioside, polypeptide, or protein. A monoclonal antibody composition thus typically displays a single binding affinity for the epitope to which it specifically binds.

Immunization

Polyclonal and monoclonal antibodies against monosialo-GM2 can be raised by immunizing a suitable subject (e.g., a hamster, rabbit, goat, mouse, or other mammal) with an immunogenic preparation which contains a suitable immunogen. Immunogens include cells such as cells from immortalized cell lines E710.2.3, RMA-S, CTLL, LB17.4, A20, WEHI-231, PBK101A2, C2.3, B16, MC57, WOP-3027, 293T, 143Btk, Jurkat, or Cos, that have all been shown to express monosialo-GM2. Alternatively, the immunogen can be purified or isolated monosialo-GM2.

The antibodies raised in the subject can then be screened to determine if the antibodies bind to fetal thymocytes while not binding to adult thymocytes. Such antibodies can be further screened in the assays described herein. For example, these antibodies can be assayed to determine if they inhibit cell proliferation of cells to which they bind; induce homotypic aggregation of cells; and/or induce apoptosis in cells to which they bind. Suitable methods to identify an antibody with the desired characteristics are described herein. For example, the ability of an antibody to induce cell death upon binding to a cell can be assayed using commercially available kits from R&D (Minneapolis, Minn.) or Pharmingen (San Diego, Calif.).

The unit dose of immunogen (e.g., purified monosialo-GM2, tumor cell expressing monosialo-GM2) and the immunization regimen will depend upon the subject to be immunized, its immune status, and the body weight of the subject. To enhance an immune response in the subject, an immunogen can be administered with an adjuvant, such as Freund's complete or incomplete adjuvant.

Immunization of a subject with an immunogen as described above induces a polyclonal antibody response. The antibody titer in the immunized subject can be monitored over time by standard techniques such as an ELISA using an immobilized antigen, e.g., monosialo-GM2.

Other methods of raising antibodies against monosialo-GM2 include using transgenic mice which express human immunoglobin genes (see, e.g., Wood et al. PCT publication WO 91/00906, Kucherlapati et al. PCT publication WO 91/10741; or Lonberg et al. PCT publication WO 92/03918). Alternatively, human monoclonal antibodies can be produced by introducing an antigen into immune deficient mice that have been engrafted with human antibody-producing cells or tissues (e.g., human bone marrow cells, peripheral blood lymphocytes (PBL), human fetal lymph node tissue, or hematopoietic stem cells). Such methods include raising antibodies in SCID-hu mice (see Duchosal et al. PCT publication WO 93/05796; U.S. Pat. No. 5,411,749; or McCune et al. (1988) *Science* 241:1632-1639)) or Rag-1/Rag-2 deficient mice. Human antibody-immune deficient mice are also commercially available. For example, Rag-2 deficient mice are available from Taconic Farms (Germantown, N.Y.).

Hybridomas

Monoclonal antibodies can be generated by immunizing a subject with an immunogen. At the appropriate time after immunization, e.g., when the antibody titers are at a sufficiently high level, antibody producing cells can be harvested from an immunized animal and used to prepare monoclonal antibodies using standard techniques. For example, the antibody producing cells can be fused by standard somatic cell fusion procedures with immortalizing cells to yield hybridoma cells. Such techniques are well known in the art, and include, for example, the hybridoma technique as originally developed by Kohler and Milstein, (1975) *Nature*, 256: 495-497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77-96). The technology for producing monoclonal antibody hybridomas is well known.

Monoclonal antibodies can also be made by harvesting antibody producing cells, e.g., splenocytes, from transgenic mice expressing human immunogloulin genes and which have been immunized with monosialo-GM2. The splenocytes can be immortalized through fusion with human myelomas or through transformation with Epstein-Barr virus (EBV). These hybridomas can be made using human B cell- or EBV-hybridoma techniques described in the art (see, e.g., Boyle et al., European Patent Publication No. 0 614 984).

Hybridoma cells producing a monoclonal antibody which specifically binds to monosialo-GM2 are detected by screening the hybridoma culture supernatants by, for example, screening to select antibodies that specifically bind to the immobilized monosialo-GM2, or by testing the antibodies as described herein to determine if the antibodies have the desired characteristics, e.g., the ability to inhibit cell proliferation.

Hybridoma cells that produce monoclonal antibodies that test positive in the screening assays described herein can be cultured in a nutrient medium under conditions and for a time sufficient to allow the hybridoma cells to secrete the monoclonal antibodies into the culture medium, to thereby produce whole antibodies. Tissue culture techniques and culture media suitable for hybridoma cells are generally described in the art (see, e.g., R. H. Kenneth, in *Monoclonal Antibodies: A New Dimension In Biological Analyses*, Plenum Publishing Corp., New York, N.Y. (1980). Conditioned hybridoma culture supernatant containing the antibody can then be collected.

Recombinant Combinatorial Antibody Libraries

Monoclonal antibodies can be engineered by constructing a recombinant combinatorial immunoglobulin library and screening the library with monosialo-GM2. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Briefly, the antibody library is screened to identify and isolate phages that express an antibody that specifically binds to monosialo-GM2. In a preferred embodiment, the primary screening of the library involves screening with an immobilized monosialo-GM2.

Following screening, the display phage is isolated and the nucleic acid encoding the selected antibody can be recovered from the display phage (e.g., from the phage genome) and subcloned into other expression vectors by well known recombinant DNA techniques. The nucleic acid can be further manipulated (e.g., linked to nucleic acid encoding additional immunoglobulin domains, such as additional constant regions) and/or expressed in a host cell.

Chimeric and Humanized Antibodies

Recombinant forms of antibodies, such as chimeric and humanized antibodies, can also be prepared to minimize the response by a human patient to the antibody. When antibodies produced in non-human subjects or derived from expression of non-human antibody genes are used therapeutically in humans, they are recognized to varying degrees as foreign, and an immune response may be generated in the patient. One approach to minimize or eliminate this immune reaction is to produce chimeric antibody derivatives, i.e., antibody molecules that combine a non-human animal variable region and a human constant region. Such antibodies retain the epitope binding specificity of the original monoclonal antibody, but may be less immunogenic when administered to humans, and therefore more likely to be tolerated by the patient.

Chimeric monoclonal antibodies can be produced by recombinant DNA techniques known in the art. For example, a gene encoding the constant region of a non-human antibody molecule is substituted with a gene encoding a human constant region (see Robinson et al., PCT Patent Publication PCT/US86/02269; Akira, et al., European Patent Application 184,187; or Taniguchi, M., European Patent Application 171, 496).

A chimeric antibody can be further "humanized" by replacing portions of the variable region not involved in antigen binding with equivalent portions from human variable regions. General reviews of "humanized" chimeric antibodies are provided by Morrison, S. L. (1985) *Science*, 229:1202-1207 and by Oi et al. (1986) *BioTechniques*, 4:214. Such methods include isolating, manipulating, and expressing the nucleic acid sequences that encode all or part of an immunoglobulin variable region from at least one of a heavy or light chain. The cDNA encoding the humanized chimeric antibody, or fragment thereof, can then be cloned into an appropriate expression vector. Suitable "humanized" antibodies can be alternatively produced by (complementarity determining region (CDR) substitution (see U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060).

Epitope imprinting can also be used to produce a "human" antibody polypeptide dimer that retains the binding specificity of the hamster antibodies specific for monosialo-GM2 produced by the hybridoma deposited as ATCC Accession No. PTA-377, Accession No. PTA-405, or Accession No. PTA-404. Briefly, a gene encoding a non-human variable region (VH) with specific binding to an antigen and a human constant region (CH1), is expressed in *E. coli* and infected with a phage library of human VκCκ genes. Phage displaying antibody fragments are then screened for binding to monosialo-GM2. Selected human Vκ genes are recloned for expression of VκCκ chains and *E. coli* harboring these chains are infected with a phage library of human VHCH1 genes and the library is subject to rounds of screening with antigen coated tubes. See Hoogenboom et al. PCT publication WO 93/06213.

Chimeric Anti-Monosialo-GM2 Antibodies

Among other things, the present invention provides chimeric antibodies that are highly specific for monosialo-GM2. These chimeric anti-monosialo-GM2 antibodies ("ChGM2 mAb") are effective at inducing apoptosis in tumor cell monolayers and/or single-cell suspensions and in inhibiting the in vivo proliferation of tumor cells.

As part of the present invention, it was determined that several hamster monoclonal antibodies specifically recognize the ganglioside monosialo-GM2. This ganglioside is present on the surface of many tumor cells. In general, the ChGM2 antibodies of the present invention have the respective Fab and CDR regions from the hamster mAbs designated DMF 10.62.3 and DMF 10.167.4. A chimeric anti-monosialo-GM2 antibody of the present invention can also have Fab or CDR regions of the hamster mAb designated DMF 10.34.36. Also provided are methods of using these chimeric anti-monosialo-GM2 antibodies in the treatment of cancer.

The present invention provides chimeric anti-monosialo-GM2 antibodies that exhibit tumor cell-specific binding and that both induce apoptosis and inhibit proliferation in the cells to which they bind. An antibody, or antigen-binding fragment thereof, is said to "specifically bind," "immunogically bind," and/or is "immunologically reactive" to monosialo-GM2 if it reacts at a detectable level (within, for example, an ELISA assay) to monosialo-GM2, but not to asialo-GM2, disialo-GM2, monosialo-GM3, disialo-GD1a, disialo-GD1b, asialo-GM1, monosialo-GM1, lysosialo-GM1, trisialo-GT1b, and/or disialo-GD3.

"Immunological binding," as used herein, generally refers to the non-covalent interactions of the type that occurs between an antibody, or fragment thereof, and an antigen for which the antibody is specific. Immunological binding properties of selected antibodies can be quantified using methods well known in the art. See, generally, Davies et al. Annual Rev. Biochem. 59:439-473 (1990).

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FWRs". Thus, the term "FWR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementary determinant region," or "CDRs."

A monoclonal antibody may be cleaved into various fragments by methods known in the art. The proteolytic enzyme papain preferentially cleaves IgG molecules to yield several fragments, two of which (the "Fab" fragments) each comprise a covalent heterodimer that includes an intact antigen-binding site. Another fragment produced from papain cleavage of an antibody is the Fc (fragment crystallizable). The Fc fragment is constant among a given class of antibodies and mediates binding of a cell or complement to an antibody when the antigen binding sites (Fabs) are occupied by an antigen.

The Fc regions are particularly constant within a given species. When a therapeutic monoclonal antibody from a first species is administered to a second species, the immune system of the second species may mount an immune response to the Fc region of the mAb. Such an immune response can lead to the rapid destruction and clearing of the mAb from the second species. Such clearing can limit the efficacy of a therapeutic antibody.

The chimeric mAbs of the present invention have a Fab portion that is derived from a hamster mAb that specifically binds to monosialo-GM2 on tumor cells. The Fc region of this hamster antibody is replaced with the Fc region of a human antibody, which limits undesirable immunological response toward non-human antibodies.

Antibodies and antigen-binding fragments have a heavy chain and a light chain complementary determinant region (CDR) set, which are respectively interposed between a heavy chain and a light chain FWR set that provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FWR set" refers to the four flanking amino acid sequences that frame the CDRs of a CDR set of a heavy or light chain V region. Some FWR residues may contact bound antigen; however, FWRs are primarily responsible for folding the V region into the antigen-binding site. The FWR residues directly adjacent to the CDRs are particularly important for the folding of the V region. Within FWRs, certain amino acid residues and certain structural features are very highly conserved. In this regard, all V region sequences contain an internal disulfide loop of around 90 amino acid residues. When the V regions fold into a binding-site, the CDRs are displayed as projecting loop motifs, which form an antigen-binding surface. It is generally recognized that there are conserved structural regions of FWRs that influence the folded shape of the CDR loops into certain "canonical" structures, regardless of the precise CDR amino acid sequence. Further, certain FWR residues are known to participate in non-covalent interdomain contacts which stabilize the interaction of the antibody heavy and light chains.

Both the light chain and heavy chain variable regions of the chimeric anti-monosialo-GM2 antibodies have three complementary determinant regions, CDRs, joined by framework regions, FWR. A ChGM2 monoclonal antibody of the present invention may have a heavy chain CDR1 with an amino acid sequence of THYVS (SEQ ID NO: 18), a heavy chain CDR 2 with an amino acid sequence of WIFGGSARTNYNQKFQG (SEQ ID NO: 17), and a heavy chain CDR3 with an amino acid sequence of QVGWDDALDF (SEQ ID NO: 16). Additionally, the ChGM2 mAb may have a light chain CDR1 with an amino acid sequence of RSSQSLFSGNYNYLA (SEQ ID NO: 15), a heavy chain CDR 2 with an amino acid sequence of YASTRHT (SEQ ID NO: 14), and a heavy chain CDR3 with an amino acid sequence of QQHYSSPRT (SEQ ID NO: 13).

Humanized Antibodies

In addition to the chimeric antibodies made for the present invention, other humanized antibodies may be produced that reduce the undesirable immunological response toward non-human antibodies in a human patient. These humanized antibody molecules can have an antigen-binding site derived from the hamster antibodies. For example, the non-human CDRs described above, can be grafted into human FWR and fused to a human constant domain. Winter et al. Nature 349: 293-299 (1991); Lobuglio et al. Proc. Nat. Acad. Sci. USA 86:4220-4224 (1989); Shaw et al. J Immunol. 138:4534-4538 (1987); and Brown et al. Cancer Res. 47:3577-3583 (1987). The hamster CDRs may be grafted into a human supporting FWR prior to fusion with an appropriate human antibody constant domain. Riechmann et al. Nature 332:323-327 (1988); Verhoeyen et al. Science 239:1534-1536 (1988); and Jones et al. Nature 321:522-525 (1986). Non-human CDRs can be supported by recombinantly-veneered FWRs. European Patent Publication No. 519,596, published Dec. 23, 1992. These "humanized" molecules are designed to minimize unwanted immunological response toward non-human antihuman antibody molecules that limits the duration and effectiveness of therapeutic applications of those moieties in human recipients. Similarly, "primatized" antibodies are designed to minimize unwanted immunological response toward non-primate anti-primate antibody molecules tht limits the duration and effectiveness of therapeutic applications of those moieties in primate recipients (e.g., humans, chimpanzees, gorillas, orangutans, etc.).

The terms "veneered FWRs" and "recombinantly veneered FWRs" refer to the selective replacement of FWR residues from, e.g., a hamster heavy or light chain V region, with human FWR residues in order to provide a xenogeneic molecule comprising an antigen-binding site which retains substantially all of the native FWR folding structure. Veneering techniques are based on the understanding that the ligand-binding characteristics of an antigen-binding site are determined primarily by the structure and relative disposition of the heavy and light chain CDR sets within the antigen-binding surface (Davies et al. Ann. Rev. Biochem. 59:439-473 (1990)). Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FWR residues, which are readily encountered by the immune system, are selectively replaced with human residues to provide a hybrid molecule that comprises either a weakly immunogenic, or substantially non-immunogenic, veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and non-human antibody fragments.

There are two general steps in veneering a non-human antigen-binding site. Initially, the FWRs of the variable domains of an antibody molecule of interest are compared with corresponding FWR sequences of human variable domains available databases. The most homologous human V regions are then compared residue by residue to corresponding non-human amino acids. The residues in the non-human FWR that differ from the human counterpart are replaced by the residues present in the human moiety using recombinant techniques well known in the art. Residue switching is carried out with moieties that are at least partially exposed (solvent accessible), and care is exercised in the replacement of amino acid residues that may have a significant effect on the tertiary structure of V region domains, such as proline, glycine and charged amino acids.

In this manner, the resultant "veneered" non-human antigen-binding sites are thus designed to retain the non-human CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FWRs which are believed to influence the "canonical" tertiary structures of the CDR loops. These design criteria are then used to prepare recombinant nucleotide sequences that combine the CDRs of both the heavy and light chain of a non-human antigen-binding site into human-appearing FWRs that can be used to transfect mammalian cells for the expression of recombinant human antibodies that exhibit the antigen specificity of the non-human antibody molecule.

Antibody Fragments

The present invention encompasses new antitumor antibodies and any fragments thereof containing the active binding region of the antibody, such as Fab, F(ab')2, and Fv fragments. Such fragments can be produced from the antibody using techniques well established in the art (see, e.g., Rousseaux et al., in Methods Enzymol., 121:663-69 Academic Press, (1986)). For example, the F(ab')$_2$ fragments can be produced by pepsin digestion of the antibody molecule, and the Fab fragments can be generated by reducing the disulphide bridges of the F(ab')$_2$ fragments.

Utility of Antibodies

The antibodies described herein have a variety of uses. The antibodies can be used in vitro for diagnostic purposes to determine the presence of malignant cells in human tissues. The method involves examining a tissue sample for the presence of monosialo-GM2. For example, the tissue sample can be contacted with the monoclonal antibody produced by the hybridoma cell line ATCC Accession NO PTA-377, Accession No. PTA-405, or Accession No. PTA-404, and the ability of the antibody to specifically bind to the cells in the tissue sample is determined. Binding indicates the presence of a tumor cell. Alternatively, the antibody can also be used to screen blood samples for released antigen.

The antibodies can also be used to localize a tumor in vivo by administering to a subject an isolated antibody of the present invention that is labeled with a reporter group which gives a detectable signal. The bound antibodies are then detected using external scintigraphy, emission tomography, or radionuclear scanning. The method can be used to stage a cancer in a patient with respect to the extent of the disease and to monitor changes in response to therapy.

The antibodies also have therapeutic applications. The new antibodies can be used to treat tumors, because specific binding of the antibody to the tumor cell causes the cell to stop proliferating and to die. The antibodies of the invention can be used to treat myeloma, small cell lung carcinoma, or melanoma. They can be used to treat other cancers, e.g., hematological malignancies, breast cancers, ovarian cancers, uterine cancers, lung cancers, GI cancers (including those affecting the oropharynx, esophagus, stomach, small and large intestine, rectum), pancreatic cancer, liver cancer, biliary cancers, kidney cancer, skin cancers, adrenal cancers, endocrine cancers, brain cancers, neural cancers, bladder cancer, bone cancer, connective tissue cancers, squamous cell carcinoma, adenocarcinoma, and mesothelioma, provided that the cancer expresses or over-expresses monosialo-GM2.

The antibodies can also be used therapeutically, e.g., as targeting agents, to deliver antitumor agents to the tumors. Such anti-tumor agents include chemotherapeutic drugs, toxins, immunological response modulators, enzymes, and radioisotopes.

Detectable Labels

The antibodies that react with monosialo-GM2 can be used diagnostically, e.g., to detect the presence of a tumor in a sample in vitro, or to locate and/or image a tumor in a subject. Detection can be facilitated by coupling the antibody to a detectable label. Examples of detectable labels include various enzymes, prosthetic groups, fluorescent materials, luminescent materials, bioluminescent materials, electron dense labels, labels for MRI, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies as Targeting Agents

The antibodies and antibody fragments described herein can be conjugated to a moiety and the antibody can be used to direct the moiety to the site of a tumor cell which expresses monosialo-GM2. Examples of moieties include toxins, radionuclides, or chemotherapeutic agents which can be used to kill tumor cells, or imaging agents which can be used to locate and size tumors expressing monosialo-GM2. The antibodies used to direct the moiety to the tumor in humans are preferably monoclonal antibodies, e.g., a humanized monoclonal antibodies.

The antibody can be fused to the moiety, e.g., the toxin, either by virtue of the moiety and the antibody being encoded by a fused gene which encodes a hybrid protein molecule, or by means of conjugation, e.g., a non-peptide covalent bond, e.g., a non-amide bond, which is used to join separately produced antibody and the moiety.

The antibody described herein can also be fused to another antibody that is specific for immune cells and stimulates the immune cells to kill the tumor.

Toxins

Useful toxin molecules that can be linked to the new antibodies include peptide toxins, which are significantly cytotoxic when present intracellularly. "Linked" mean attached or bound covalently or non-covalently with a bond that cannot by disrupted under normal physiological conditions for at least 24 hours. Examples of other toxins include cytotoxins, metabolic disrupters (inhibitors and activators) that disrupt enzymatic activity and thereby kill tumor cells, and radioactive molecules that kill all cells within a defined radius of the effector portion. A metabolic disrupter is a molecule, e.g., an enzyme or a cytokine, that changes the metabolism of a cell such that its normal function is altered. Broadly, the term toxin includes any effector that causes death to a tumor cell.

Many peptide toxins have a generalized eukaryotic receptor binding domain; in these instances the toxin must be modified to prevent killing cells not bearing the targeted protein (e.g., to prevent killing of cells not bearing monosialo-GM2 but having a receptor for the unmodified toxin). Such modifications must be made in a manner that preserves the cytotoxic function of the molecule. Potentially useful toxins include, but are not limited to: diphtheria toxin, cholera toxin, ricin, α-Shiga-like toxin (SLT-I, SLT-II, SLT-II$_v$), LT toxin, C3 toxin, Shiga toxin, pertussis toxin, tetanus toxin, *Pseudomonas* exotoxin, alorin, saponin, modeccin, and gelanin. Other toxins include tumor necrosis factor alpha (TNF-α) and lymphotoxin (LT). Another toxin which has antitumor activity is calicheamicin gamma 1, a diyne-ene containing antitumor antibiotic with considerable potency against tumors (Zein, N., et al., *Science*, 240:1198-201 (1988)).

As an example, diphtheria toxin can be conjugated to the antibodies described herein. Diphtheria toxin, whose sequence is known, is described in detail in Murphy, U.S. Pat. No. 4,675,382, which is incorporated herein by reference. The natural diphtheria toxin molecule secreted by *Corynebacterium diphtheriae* consists of several functional domains that can be characterized, starting at the amino terminal end of the molecule, as enzymatically-active Fragment A (amino acids $Gly_1$-$Arg_{193}$) and Fragment B (amino acids $Ser_{194}$-$Ser_{535}$), which includes a translocation domain and a generalized cell binding domain (amino acid residues 475 through 535).

Linkage of Toxins to Antibodies

The antibody and the toxin moiety can be linked in any of several ways. If the compound is produced by expression of a fused gene, a peptide bond serves as the link between the cytotoxin and the antibody. Alternatively, the toxin and the antibody can be produced separately and later coupled by means of a non-peptide covalent bond. For example, the covalent linkage may take the form of a disulfide bond. In this case, the DNA encoding this antibody can be engineered, by conventional methods, to contain an extra cysteine codon.

For a disulfide bond linkage, the toxin molecule is also derivatized with a sulfhydryl group reactive with the cysteine of the modified antibody. In the case of a peptide toxin this linkage can be accomplished by inserting a cysteine codon into the DNA sequence encoding the toxin. Alternatively, a sulfhydryl group, either by itself or as part of a cysteine residue, can be introduced using solid phase polypeptide techniques. For example, the introduction of sulfhydryl groups into peptides is described by Hiskey, *Peptides*, 3:137 (1981).

Derivatization can also be carried out according to the method described for the derivatization of a peptide hormone in Bacha et al., U.S. Pat. No. 4,468,382. The introduction of sulfhydryl groups into proteins is described in Maasen et al., *Eur. J. Biochem.*, 134:32 (1983). Once the required sulfhydryl groups are present, the cytotoxin and the antibody are purified, both sulfur groups are reduced, cytotoxin and antibody are mixed (in a ratio of about 1:5 to 1:20), and disulfide bond formation is allowed to proceed to completion (generally 20 to 30 minutes) at room temperature. The mixture is then dialyzed against phosphate buffered saline to remove unreacted antibody and toxin molecules. Sephadex® chromatography or the like is used to separate the desired toxin-antibody conjugate compounds from toxin-toxin and antibody-antibody conjugates on the basis of size.

Immune Response Modulators

The antitumor moiety can also be a modulator of the immune system that either activates or inhibits the body's immune system at the local level. For example, cytokines, e.g., lymphokines such as IL-2, delivered to a tumor can cause the proliferation of cytotoxic T-lymphocytes or natural killer cells in the vicinity of the tumor.

Radioactive Molecules

The moiety or reporter group can also be a radioactive molecule, e.g., a radionucleotide, or a so-called sensitizer, e.g., a precursor molecule, that becomes radioactive under specific conditions, e.g., boron when exposed to a beam of low-energy neutrons, in the so-called "boron neutron capture therapy" (BNCT). Barth et al., *Scientific American*, October 1990:100-107 (1990). Compounds with such radioactive effector portions can be used both to inhibit tumor cell proliferation and to label the tumor cells for imaging purposes.

Radionuclides are single atom radioactive molecules that can emit either α, β, or γ particles. Alpha particle emitters are preferred to β or Ü particle emitters, because they release far higher energy emissions over a shorter distance, and are therefore efficient without significantly penetrating, and harming, normal tissues. Suitable Ó particle emitting radionuclides include $^{211}At$, $^{212}Pb$, and $^{212}Bi$.

The radioactive molecule must be tightly linked to the antibody, e.g., either directly or by a bifunctional chelate. This chelate must not allow elution and thus premature release of the radioactive molecule in vivo. (see, e.g., Waldmann, *Science*, 252:1657-62 (1991)).

For example, to adapt BNCT to the present invention, a stable isotope of boron, e.g., boron 10, is selected as the antitumor moiety or effector portion of the compound. The boron is delivered to and concentrates in or on the tumor cells by the specific binding of the antibody to the tumor cell. After a time that allows a sufficient amount of the boron to accumulate, the tumor is imaged and irradiated with a beam of low-energy neutrons, having an energy of about 0.025 eV. While this neutron irradiation, by itself, causes little damage to either the healthy tissue surrounding the tumor, or the tumor itself, boron 10 (e.g., on the surface of a tumor cell) captures the neutrons, thereby forming an unstable isotope, boron 11. Boron 11 instantly fissions yielding lithium 7 nuclei and energetic Ó particles, about 2.79 million Ev. These heavy particles are a highly lethal, but very localized, form of radiation, because particles have a path length of only about one cell diameter (10 microns).

Calculations have shown that to destroy a tumor cell, about one billion boron atoms are required along with a flow of thermal neutrons of from $10^{12}$ to $10^{13}$ neutrons per square centimeter, so that the radiation generated by the Ó particles exceeds the background radiation generated by neutron capture reactions with nitrogen and hydrogen.

Imaging Moieties

The antibodies described herein specifically bind to monosialo-GM2 and are thus also useful to detect and/or image human tumors. One such approach involves the detection of tumors in vivo by tumor imaging techniques using the antibody labeled with an appropriate moiety or reporter group, e.g., an imaging reagent that produces a detectable signal. Imaging reagents and procedures for labeling antibodies with such reagents are well known (see, e.g., Wensel and Meares, Radio Immunoimaging and Radioimmunotherapy, Elsevier, N.Y. (1983); Colcher et al., Meth. Enzymol., 121:802-16 (1986)). The labeled antibody can be detected by a technique such as radionuclear scanning (see, e.g., Bradwell et al. in Monoclonal Antibodies for Cancer Detection and Therapy, Baldwin et al. (eds.), pp. 65-85, Academic Press (1985)), or magnetic resonance imaging.

Administration

The antibodies described herein can be administered to a subject, e.g., an animal or a human, to image or treat tumors. The antibodies can be administered alone, or in a mixture, e.g., in the presence of a pharmaceutically acceptable excipient or carrier (e.g., physiological saline). The excipient or carrier is selected on the basis of the mode and route of administration. Suitable pharmaceutical carriers are described in *Remington's Pharmaceutical Sciences* (E. W. Martin), a well known reference text in this field, and in the USP/NF (United States Pharmacopeia and the National Formulary).

Pharmaceutical Compositions

In some embodiments, the present invention concerns formulation of one or more of the anti-monosialo-GM2 antibodies disclosed herein in pharmaceutically-acceptable carriers for administration to a cell or an animal, either alone, or in combination with one or more other modalities of therapy.

A pharmaceutical composition is formulated to be compatible with its intended route of administration. Examples of routes of administration include parenteral, e.g., intravenous, intradermal, subcutaneous, oral (e.g., inhalation), transdermal (e.g., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Carriers and Buffers

It will be understood that, if desired, a composition as disclosed herein may be administered in combination with other agents as well, such as, e.g., other proteins or various pharmaceutically-active agents. The compositions may thus be delivered along with various other agents as required in the particular instance. Such compositions may be purified from host cells or other biological sources, or alternatively may be chemically synthesized.

Therefore, in another aspect of the present invention, pharmaceutical compositions are provided comprising one or more of the anti-monsialo-GM2 antibodies described herein in combination with a physiologically acceptable carrier. In certain preferred embodiments, the pharmaceutical compositions of the invention include a ChGM2 mAb for use in prophylactic and/or therapeutic applications.

It will be apparent that any of the pharmaceutical compositions described herein can contain pharmaceutically acceptable salts of the anti-monosialo-GM2 antibodies. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation may provide a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, gangliosides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

Polynucleotide-Based Compositions

In another embodiment, illustrative compositions of the present invention comprise DNA encoding one or more of the anti-ganglioside antibodies as described above, such that the antibody is generated in vivo. The polynucleotide may be administered within any of a variety of delivery systems known to those of ordinary skill in the art. Indeed, numerous gene delivery techniques are well known in the art, such as those described by Rolland, Crit. Rev. Therap. Drug Carrier Systems 15:143-198, 1998, and references cited therein. Appropriate polynucleotide expression systems will, of course, contain the necessary DNA regulatory sequences for expression in a patient (such as a suitable promoter and terminating signal).

Packaging

The pharmaceutical compositions described herein may be presented in unit-dose or multi-dose containers, such as sealed ampoules or vials, along with instructions for use, e.g., to treat a specific cancer. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

Dosing, Delivery, and Treatment Regimens

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain circumstances it will be desirable to deliver the pharmaceutical compositions disclosed herein parenterally, intravenously, intramuscularly, or intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In some embodiments, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

The anti-monosialo-GM2 antibody compositions described herein may be used in therapeutic methods for the treatment of cancer. For example, a pharmaceutical composition containing the ChGM2 antibodies of the invention, may be administered to a human patient. Such pharmaceutical compositions may be administered either prior to or following surgical removal of primary tumors and/or treatment such as administration of radiotherapy or conventional chemotherapeutic drugs. Administration of the ChGM2 antibody compositions may be by any suitable method, including administration by intravenous, intraperitoneal, intramuscular, subcutaneous, intranasal, intradermal, anal, vaginal, topical and oral routes.

Anti-monosialo-GM2 specific antibodies of the present invention may be employed in passive immunotherapeutic methods. These treatment methods involve the delivery of ChGM2 antibodies that can directly or indirectly mediate antitumor effects, such as inducing apoptosis and/or inhibiting proliferation of the tumor cell to which the antibody binds. Such immunotherapeutic methods do not necessarily depend on an intact host immune system because of the anti-monosialo-GM2 antibody's ability to induce apoptosis in a tumor cell to which it binds.

Routes and frequency of administration of the therapeutic compositions of the present invention, as well as dosage, will vary from individual to individual, and may be readily established using standard techniques. In general, the pharmaceutical compositions may be administered by injection (e.g., intracutaneous, intramuscular, intravenous or subcutaneous), intranasally (e.g., by aspiration) or orally.

An appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Typically, a suitable dose is an amount of a compound that, when administered as described above, is capable of promoting an anti-tumor response, and is at least 10-50% above the basal (i.e., untreated) level.

The most effective mode of administration and dosage regimen for the compositions of this invention depend upon the severity and course of the disease, the patient's health and response to treatment, and the judgment of the treating physician. Accordingly, the dosages of the compositions should be titrated to the individual patient. An effective dose of the antibody composition of this invention is in the range of from about 1 ug to about 5000 mg, preferably about 1 to about 500 mg, or preferably about 100-200 mg.

Diagnostic Kits

The invention also encompasses diagnostic kits for carrying out the methods disclosed above. The diagnostic kit includes (a) a monoclonal antibody described herein, and (b) a conjugate of a specific binding partner for the antibody and a label for detecting bound antibody. The kit may also include ancillary agents such as buffering agents and protein stabilizing agents, e.g., polysaccharides and the like. The diagnostic kit may further include, where necessary, other components of a signal-producing system including agents for reducing background interference, control reagents, and an apparatus for conducting a test. In another embodiment, the diagnostic kit includes a conjugate of a monoclonal antibody of the invention and a label capable of producing a detectable signal. Ancillary agents as mentioned above may also be present. Instructions on how to use the diagnostic kit are generally also included.

EXAMPLES

The following examples are given to illustrate various embodiments that have been made of the present invention. It is to be understood that the following examples are not comprehensive or exhaustive of the many types of embodiments that can be prepared in accordance with the present invention.

Example 1

Biological Characterization of Hamster Monoclonal Antibody DMF 10.167.4

The hamster monoclonal antibody (mAb) DMF 10.167.4 and the clonally related antibody DMF10.62.3 bind to the cell surface of murine thymic lymphoma cells. Antibodies DMF 10.167.4 and DMF10.62.3 were derived from the same fusion. The DMF 10.167.4 mAb induces apoptosis and inhibits cellular proliferation of cells to which the antibody binds. Three hamster monoclonal antibodies (DMF 10.62.3, DMF 10.167.4, and DMF 10.34.36), were raised against E710.2.3 mouse thymic lymphoma cells, that bound to a cell surface ligand on a large number of cell lines including a few normal primary lines as well as tumor cell lines.

The DMF 10.167.4 mAb antibody was tested for ganglioside specificity. To determine ligand specificity, individual wells of ELISA plates were coated overnight, with monosialo-GM2, asialo-GM2, disialo-GM2, monosialo-GM3, disialo-GD1a, disialo-GD1b, asialo-GM1, monosialo-GM1, lysosialo-GM1, trisialo-GT1b, and disialo-GD3 gangliosides (all from Sigma; St. Louis, Mo.). Wells were blocked for 2 hours with blocking buffer (PBS+1% BSA) and incubated with primary antibodies, either DMF 10.167.4, DMF 10.62.3, or hamster immunoglobulin (Ig) as a control, diluted 1 µg/ml in blocking buffer for 1 hour. Following 5 washes in PBS, plates were incubated with goat anti-hamster Ig-HRP (Pharmingen; San Diego, Calif.) for 1 hour in PBS+1% BSA. Plates were washed in PBS and developed in TMB substrate for 10 minutes before quenching with 1M NaOH. Absorbance was measured at 450 nm-570 nm by an ELISA plate reader. (FIG. 2). These data show that the DMF 10.167.4 mAb bound specifically only to monosialo-GM2. The structurally related ganglioside monosialo-GM3, lacking 1 terminal galactose residue compared to monosialo-GM2, and monosialo-GM1, possessing one additional galactose residue, were not recognized, nor was the sialic acid deficient ganglioside asialo-GM2. These results suggest that the epitope recognized by DMF10.167.4 mAb consists of a combination of the terminal galactose sugar and the sialic acid residue. A molecular description of these gangliosides is shown in FIG. 1. Treatment of monosialo-GM2 with neuraminidase A, which cleaves off the sialic acid residue, led to a loss of DMF10.167.4 binding as measured by ELISA (data not shown), further validating the epitope specificity of this mAb.

Cell surface binding of hamster monoclonal antibody DMF 10.167.4 was determined by flow cytometric methods (i.e. FACS analysis). Single suspensions of murine thymic lymphoma cells were generated, cells were washed 3 times with ice cold staining buffer (PBS+1% BSA+Azide), and were incubated for 30 minutes on ice with 10 µg/ml of Protein A/G purified hamster mAb DMF 10.167.4. The cells were washed three times with staining buffer and then incubated with a 1:100 dilution of an anti-hamster IgG-FITC reagent (Pharmingen; San Diego, Calif.) for 30 minutes on ice. Following three washes, the cells were re-suspended in staining buffer containing Propidium Iodide (PI), a vital stain that allows for identification of permeable cells, and analyzed by FACS.

Flow cytometric analysis using the DMF10.167.4 mAb was performed to determine the extent of coverage of monosialo-GM2 surface expression on several types of human tumor cell lines. As summarized in Table 1, 90% of the SCLC lines that were tested were positive for monosialo-GM2 expression. Three lines, NCI-H69, HTB173 and HTB 180 demonstrated weak binding, as approximately 15% of cells were positive for DMF10.167.4 binding, whereas six lines, including HTB 175, HTB 171, DMS79, NCI-H128, NCI-H187, and SHP-77 demonstrated strong binding with greater than 40% of cells staining positive. The SCLC line HTB 172 was negative for monosialo-GM2 expression. For melanoma cell lines, 75% of lines tested expressed monosialo-GM2, with CHL-1, Mel S, and Mel D showing strong positive staining, whereas MTL450-5 cells were negative. In terms of monosialo-GM2 expression on the cell surface of other types of tumor cell lines, two kidney lines, HEK293 and HICK 10-4, were strongly positive, as were the Jurkat T cell and K562 B cell leukemia lines, while the HL-60 and THP-1 leukemia lines and the 721 B cell line showed no monosialo-GM2 expression. Representative lines derived from pancreas, breast, prostate, ovarian and myeloma tumors were also analyzed and demonstrated lower extents of coverage (33% to 20%) of monosialo-GM2 expression.

Neither the DMF10.167.4 mAb nor the DMF10.62.3 mAb was able to recognize monosialo-GM2 in formalin-fixed or frozen tissues by IHC analysis, suggesting that the epitope recognized by these mAbs is destroyed during the tissue preparation process. Because of this absence of epitope recognition, flow cytometry was used to analyze DMF10.167.4 mAb reactivity on normal cells obtained from Clonetics Inc. that had been dissociated from normal tissues and propagated in vitro. This analysis revealed that lung and prostate epithelium, as well as prostate stroma, human aortic and umbilical endothelium, and human PBMCs demonstrated no specific binding with this mAb. Human fibroblasts were weakly positive for monosialo-GM2 (less than 10% positive-staining cells), but were found not to apoptose when treated with the mAb in vitro (data not shown). These data confirm the overexpression of monosialo-GM2 on tumor cell lines and the relative lack of monosialo-GM2 expression on normal tissues, making this antigen an appropriate target of therapeutic mAbs.

For analysis of apoptosis induction, $2 \times 10^5$ murine thymic lymphoma cells were incubated over night with 10 μg/ml of the DMF 10.167.4 mAb or control mAbs, then assayed for annexin positivity and active caspase content by incubating the cells with an annexin V-Alexa488 conjugate (Molecular Probes; Eugene, Oreg.) or with the CaspaTag™ reagent (Intergen; Norcross, Ga.). Cells were subjected to flow cytometric analysis to determine the amount of annexin positivity or caspa-tag positivity, respectively, as measures of induced apoptotic activity.

To determine the effective of the mAb on cellular proliferation, 3000 cells/well were plated into a 96 well plate in triplicate or quadruplicate in a final volume of 200 μl media. CHL melanoma or K562 leukemia cells were allowed to adhere for at least four hrs, then 10-20 μg/ml of DMF 10.167.4 mAb or control hamster mAb was added. Cells were grown for three days, after which time 25 μCi of $^3$H-thymidine was added per well. Following a four hour incubation, cells were lysed then subjected to counting on a beta-counter to determine relative levels of $^3$H incorporation.

Surface binding, apoptosis, caspase activation, and proliferation data are shown in Table 1. These data revealed that the hamster monoclonal antibody, designated DMF 10.167.4, was capable of binding to a variety of tumor cell lines from breast, pancreas, kidney, ovary, melanoma, leukemia, prostate, and osteosarcoma. Furthermore, this antibody was effective in inducing apoptosis and caspase activity as well as in decreasing proliferation in a subset of these tumor cell lines.

TABLE 1

Ex vivo Biological Characterization of Hamster Antibody DMF 10.167.4

| Tumor | Type | Surface by FACS | Apoptosis by Annexin | Caspase Activation | Decreased Proliferation | Source |
|---|---|---|---|---|---|---|
| BT474 | Breast | – | –/na | | | ATCC; Manassas, VA |
| HTB 175 | SCLC | +++ | ++ | | | |
| HTB 171 | SCLC | +++ | | | | |
| DMS 79 | SCLC | +++ | | | | |
| NCI-H128 | SCLC | +++ | | | | |
| NCI-H1H7 | SCLC | +++ | | | | |
| SHP-77 | SCLC | +++ | | | | |
| NCI-H69 | SCLC | + | | | | |
| HTB 173 | SCLC | + | | | | |
| HTB 180 | SCLC | + | | | | |
| HTB-172 | SCLC | – | | | | |
| MB415 | Breast | + | –/na | | | ATCC; Manassas, VA |
| SKBR3 | Breast | – | | | | ATCC; Manassas, VA |
| CRL-1687 | Pancreas | – | | | | ATCC; Manassas, VA |
| CRL-1837 | Pancreas | – | – | | | ATCC; Manassas, VA |
| PCT391-34 | Pancreas | + | – | | | ATCC; Manassas, VA |
| HICK 10-4 | Renal | + | | | | ATCC; Manassas, VA |
| HEK293 | Renal | + | –/na | | | ATCC; Manassas, VA |
| OTL298-95 | Ovarian | – | | | | ATCC; Manassas, VA |

TABLE 1-continued

Ex vivo Biological Characterization of Hamster Antibody DMF 10.167.4

| Tumor | Type | Surface by FACS | Apoptosis by Annexin | Caspase Activation | Decreased Proliferation | Source |
|---|---|---|---|---|---|---|
| ES-2 | Ovarian | − | | | | ATCC; Manassas, VA |
| OV1063 | Ovarian | + | | | | ATCC; Manassas, VA |
| SKOV3 | Ovarian | − | | | | ATCC; Manassas, VA |
| CHL-1 | Melanoma | ++++ | ++/m3 | ++ | 40% (2) | ATCC; Manassas, VA |
| MTL450-5 | Melanoma | − | | | | ATCC; Manassas, VA |
| HL-60 | Leukemia | − | | | | ATCC; Manassas, VA |
| K562 | Leukemia | +++ | ++ | + | 17%, 25% | ATCC; Manassas, VA |
| THP-1 | Leukemia | − | | | | ATCC; Manassas, VA |
| Du145 | Prostate | ++ | −/na | − | | ATCC; Manassas, VA |
| LnCap | Prostate | − | | | | ATCC; Manassas, VA |
| PC-3 | Prostate | − | − | − | | ATCC; Manassas, VA |
| Mel D | Melanoma | + | − | − | | ATCC; Manassas, VA |
| Mel S | Melanoma | + | − | − | | ATCC; Manassas, VA |
| Jurkat | T Cell Leukemia | + | − | − | | ATCC; Manassas, VA |
| 721 | B Cell Leukemia | − | | | | ATCC; Manassas, VA |
| Hela | Cervical | − | | | | ATCC; Manassas, VA |
| 143BTK | Osteosareoma | + | | | | ATCC; Manassas, VA |
| RMAS | Mouse | +++ | ++ | | | ATCC; Manassas, VA |
| N. PrEpithelium | Normal Prostate | − | − | | | Clonetics; Verviers, Belgium |
| N.Pr. Stromal | Normal Prostate | − | | | | Clonetics; Verviers, Belgium |
| N.Lu. Epithelium | Normal Lung | − | − | | | Clonetics; Verviers, Belgium |
| N. Fibroblast | Mouse | + | − | | | Clonetics; Verviers, Belgium |
| Adult Spleen | Mouse | − | | | | |
| Adult Thymus | Mouse | − | | | | |
| Adult BM | Mouse | − | | | | |
| Fetal Thymus | Mouse | + | | | | |
| Activated T Cells | Mouse | − | | | | |

TABLE 1-continued

Ex vivo Biological Characterization of Hamster Antibody DMF 10.167.4

| Tumor | Type | Surface by FACS | Apoptosis by Annexin | Caspase Activation | Decreased Proliferation | Source |
|---|---|---|---|---|---|---|
| Activated B Cells | Mouse | − | | | | |

Blank cells indicate that cell line was not tested.

Example 2

Sequence Analysis of cDNA Encoding the Hamster DMF 10.167.4 mAb

To determine the heavy and light chain variable region cDNA sequences of the DMF-10.167.4 mAb total RNA was isolated from ~2 million cells by extracting the cells with Trizol reagent (Invitrogen Corp.; Carlsbad, Calif.). First strand cDNA was generated using the Advantage RT for PCR kit (BD Biosciences Clontech; Franklin Lakes, N.J.), tailed with dGTP using TdT (Invitrogen Corp.; Carlsbad, Calif.), and then used as a template for PCR amplification. The PCR was carried out using a 5' sense poly-dCTP oligo with a 3' anti-sense kappa or gamma chain constant region specific oligonucleotides for amplification of light and heavy chains, respectively. The products were subcloned into the pCR-Blunt vector (Invitrogen Corp.; Carlsbad, Calif.) and subjected to sequence analysis. Clones 10.167.4H and 10.167.4L were determined to encode the leader sequence and the heavy chain variable region (VDJ) and light chain variable region (VJ), respectively, of the DMF10.167.4 mAb. The sequences are disclosed herein as SEQ ID NOs: 12 and 11, respectively. The corresponding variable region sequences minus the endogenous leader sequences are disclosed herein as SEQ ID NOs: 10 and 9, respectively, and the corresponding amino acid sequences encoded by the above DNA sequences are disclosed herein as SEQ ID NOs: 26, 25, 24 and 23, respectively.

Example 3

Anti-Ganglioside Antibodies DMF 10.62.3 and DMF 10.167.4 are Clonally Related

The DMF10.62.3 antibody disclosed and characterized in U.S. patent application Ser. No. 09/618,421 is clonally related (i.e. derived from the same parental B cell clone) to the DMF10.167.4 antibody disclosed therein and further characterized herein and, as a consequence thereof, both of these antibodies share functional properties of antigen binding specificity and affinity.

The nucleotide sequences of the immunoglobulin heavy and light chains of the anti-monosialo-GM2 hamster mAb DMF10.62.3 were determined and compared to the corresponding sequences of hamster mAb DMF10.167.4. Approximately two million DMF10.62.3 hybrid cells were used to isolate mRNA using Tri-reagent (Gibco; San Diego, Calif.). First strand cDNA synthesis was carried out using the Advantage RT for PCR kit (BD Biosciences Clontech; Franklin Lakes, N.J.). PCR amplification was performed using specific constant region and degenerate consensus leader oligonucleotides primers provided in the Ig-prime kit (Novagen, Inc.; Madison, Wis.). PCR products were subcloned into the pCR-Blunt vector (Invitrogen Corp.; Carlsbad, Calif.) and subjected to sequencing analysis. Clones 10.62.3L and 10.62.3H were determined to encode the light variable region (VJ) and heavy variable region (VDJ), respectively, of the DMF10.62.3 mAb. These sequence of the light chain and heavy chain variable regions of the DMF10.167.4 mAb were compared to another hamster mAb, DMF10.62.3, which also was determined to bind to monosialo-GM2.

The amino acid sequence of the VJ and VDJ of DMF10.62.3 are disclosed as SEQ ID NOS: 19 and 20 respectively. The nucleotide sequence of the VJ and the VDJ of DMF10.62.3 are disclosed as SEQ ID NOS: 5 and 6 respectively. The sequence of DMF10.62.3 and DMF10.167.4 were substantially similar with a single residue change in the light chain variable region and a single residue change in the heavy chain variable region. The isoleucine at linear position 52 of the of the light chain variable region of DMF10.167.4 as defined in SEQ ID NO: 23 is replaced with valine in SEQ ID NO: 19, and the threonine at linear position 78 of the heavy chain variable region of DMF10.167.4 as defined in SEQ ID NO: 24 is replaced with lysine in SEQ ID NO: 20. These modifications are not within the CDRs of the hamster antibodies.

The near identity of the variable regions and identity of CDR3 confirm that the DMF10.62.3 and DMF10.167.4 mAbs are clonally related and, consequently, share functional properties such as antigen binding specificity and affinity.

Example 4

Comparison of DMF10.167.4 mAb and L6-20-4 mAb Ligand Specificity

The ligand specificity of the anti-monosialo-GM2 specific hamster antibody, DMF10.167.4, is distinct from that of the anti-asialo-GM2 specific mouse antibody, L6-20-4 (ATCC No. HB-8677) described in U.S. Pat. Nos. 4,935,495 and 5,091,177 to Hellstrom, et al. The specificity of the DMF10.167.4 mAb was further characterized by flow cytometry and ELISA and shown to be different than the specificity of the anti-asialo-GM2 L6-20-4 mAb.

For flow cytometric analysis single cell suspensions of HEK and CHL-1 cells were generated. Cells were then washed 3 times with ice cold staining buffer (PBS+1% BSA+ azide). Next, the cells were incubated for 30 minutes on ice with DMF10.167.4 supernatant or 16-20-4 supernatant. The cells were washed 3 times with staining buffer and then incubated with a 1:100 dilution of an anti-hamster IgG-FITC reagent (Pharmingen; San Diego, Calif.) or anti-mouse IgG-FITC (Southern Biotech; Birmingham, Ala.) for 30 minutes on ice. Following 3 washes, the cells were resuspended in staining buffer containing Propidium Iodide (PI), a vital stain that allows for identification of permeable cells, and analyzed by flow cytometry. The DMF10.167.4 mAb recognized both HEK and CHL-1 cells by FACS as demonstrated by the increase in the mean fluorescent intensity (MFI) of ~30 for DMF 10.167.4 mAb vs. Hamster Ig MFI~3 for both HEK and CHL cells whereas L6-20-4 mAb bound CHL-1 cells (MFI~40 vs. irrelevant mouse Ig MFI~3) but not HEK cells (MFI~3 vs irrelevant mouse Ig MFI~3) demonstrating that the antibody has binding activity.

For ELISA analysis monosialo-GM3, monosial-GM2, and asialo-GM2 were coated onto wells of 96 well plates at 0.5 μg/well in chloroform/methanol. Wells were blocked for 2 hours with PBS+1% BSA and incubated with primary antibody supernatants, either DMF 10.167.4 or the L6-20-4 mAb, for 1 hour. Following 5 washes in PBS, plates were incubated with goat anti-hamster or goat anti-mouse Ig-HRP (Pharmingen; San Diego, Calif.) for 1 hour. Plates were washed in PBS and developed in TMB substrate for 10 minutes before quenching with 1M NaOH. Absorbance was measured at 450 nm-570 nm by an ELISA plate reader. These results demonstrate that DMF10.167.4 specifically bound monosialo-GM2 ($OD_{450}$ 2.64 vs $OD_{450}$=0.099 for monosialo-GM3 and 0.139 for asialo-GM2 and 0.159 for methanol) whereas L6-20-4 showed no specific binding to monosialo-GM2 ($OD_{450}$=0.032 for methanol, 0.0245 for monosialo-GM3, 0.026 for monosialo-GM2, and 0.03 for asialo-GM2). These data collectively confirmed that the DMF10.167.4 mAb bound specifically to monosialo-GM2, and is of a different specificity than that of the L6-20-4 mAb.

Example 5

The In Vivo Effect of the DMF10.62.3 Antibody

AKR mice were injected IV or IP with $5 \times 10^6$ syngeneic E710.2.3 tumor cells and received saline or an injection IP of 0.5 mg of control hamster antibody or DMF10.62.3 antibody on the initial day and again 10 days later. The survival of animals was followed for 50 days (Table 2). These data show that the DMF10.62.3 mAb can block tumor formation and prolong viability in vivo.

TABLE 2

| Treatment | Survival | Average time to death |
| --- | --- | --- |
| 1. saline | 0% | 35 days |
| 2. control antibody | 0% | 33 days |
| 3. DMF62.3 | 100% | (No deaths) |

Example 6

Human Myeloma Cell-Surface Binding by DMF10.167.4 mAb

To determine if monosialo-GM2 is expressed on the surface of myeloma cells and recognized by the DMF10.167.4 mAb, $1 \times 10^6$ cells were incubated with 10 μg/ml irrelevant hamster IgG or DMF10.167.4 mAb on ice, then washed 3 times with staining buffer (PBS+1% BSA+Azide). Cells were then incubated with FITC-conjugated anti-hamster IgG on ice, and then washed 3 times with staining buffer. Cells were resuspended in staining buffer containing propidium iodide, a vital stain that distinguishes permeable cells from viable cells, then analyzed by flow cytometry. As demonstrated by the increase in the mean fluorescent intensity (MFI) values of the DMF10.167.4 mAb compared to irrelevant hamster IgG, which is a measurement of the relative binding ability, the DMF10.167.4 mAb was shown to recognize and bind to monosialo-GM2 on the surface of several human myeloma cell lines, including DP-6 (Irrelevant: 3.03 vs. DMF10.167.4:93.81), OPM-2 (2.82 vs. 488.1), U266 (1.86 vs. 232.7), RPMI-8226 (6.14 vs. 150.8) and NCI-H929 (4.2 vs. 62.7). These data indicate that the DMF10.167.4 mAb recognizes monosialo-GM2 on a number of myeloma cell lines and suggest that the mAb could be used for the therapeutic treatment of multiple myeloma.

Example 7

Apoptosis of Human Myeloma Cells by DMF10.167.4 mAb Treatment

To demonstrate the apoptotic potential of the DMF10.167.4 mAb on myeloma cells, $2 \times 10^5$ U-266 cells were plated and incubated O/N with 20 μg/ml of the anti-DMF10.167.4 mAb or irrelevant hamster IgG, then assayed for annexin positivity and active caspase content by incubating the cells with an annexin V-Alexa488 conjugate (Molecular Probes). Cells were subjected to flow cytometric analysis to determine the amount of annexin positivity as a measure of DMF10.167.4 mAb-induced apoptotic activity. The irrelevant hamster IgG revealed a background of 9.6% apoptosis, whereas the DMF10.167.4 mAb was responsible for inducing 31.3% of the cells to undergo apoptosis, a greater than 3-fold increase. These data indicate that the hamster anti-monosialo-GM2 mAb could be used as a therapeutic antibody by targeting monosialo-GM2 on myeloma tumors.

Example 8

Human Melanoma Cell Surface Binding by DMF10.167.4 mAb

To determine if monsialo-GM2 is expressed on the surface of melanoma cells and recognized by the DMF10.167.4 mAb, $1 \times 10^6$ CHL-1 cells were incubated with 10 μg/ml irrelevant hamster IgG or DMF10.167.4 mAb on ice, then washed 3 times with staining buffer (PBS+1% BSA+Azide). Cells were then incubated with FITC-conjugated anti-hamster IgG on ice, and then washed 3 times with staining buffer. Cells were resuspended in staining buffer containing propidium iodide, a vital stain that distinguishes permeable cells from viable cells, then analyzed by flow cytometry. As demonstrated by the increase in the mean fluorescent intensity (MFI) values of the DMF10.167.4 mAb compared to irrelevant hamster IgG, which is a measurement of the relative binding ability, the DMF10.167.4 mAb was shown to recognize and bind to monosialo-GM2 on the surface of the CHL-1 melanoma cell line (Irrelevant: 3.2 vs. DMF10.167.4:~100). These data indicate that the DMF10.167.4 mAb recognizes monosialo-GM2 on melanoma cells and suggest that the mAb could be used for the therapeutic treatment of melanoma.

Example 9

Apoptosis of Human Melanoma Cells by DMF10.167.4 mAb Treatment

To demonstrate the apoptotic potential of the DMF10.167.4 mAb on melanoma cells, $2 \times 10^5$ CHL-1 cells were plated and incubated O/N with 20 μg/ml of the DMF10.167.4 mAb or irrelevant hamster IgG, then assayed for annexin positivity and active caspase content by incubating the cells with an annexin V-Alexa488 conjugate (Molecular Probes). Cells were subjected to flow cytometric analysis to determine the amount of annexin positivity as a measure of DMF10.167.4 mAb-induced apoptotic activity. The irrelevant hamster IgG revealed a background of 4.6% apoptosis, whereas the DMF10.167.4 mAb was responsible for inducing 42.1% of the cells to undergo apoptosis, a greater than 9-fold increase. These data indicate that the hamster anti-monosialo-GM2 mAb could be used as a therapeutic antibody by targeting monosialo-GM2 on melanoma tumors.

Example 10

Human Small Cell Lung Cancer (SCLC) Surface Binding by DMF10.167.4 mAb

To determine if monosialo-GM2 is expressed on the surface of SCLC cells and recognized by the DMF10.167.4 mAb, $1 \times 10^6$ cells from numerous SCLC cell lines were incubated with 10 µg/ml irrelevant hamster IgG or DMF10.167.4 mAb on ice, then washed 3 times with staining buffer (PBS+ 1% BSA+Azide). Cells were then incubated with FITC-conjugated anti-hamster IgG on ice, and then washed 3 times with staining buffer. Cells were resuspended in staining buffer containing propidium iodide, a vital stain that distinguishes permeable cells from viable cells, then analyzed by flow cytometry. As demonstrated by the increase in the mean fluorescent intensity (MFI) values of the DMF10.167.4 mAb compared to irrelevant hamster IgG, which is a measurement of the relative binding ability, the DMF10.167.4 mAb was shown to recognize and bind to monosialo-GM2 on the surface of the SCLC cell lines, including NCI-H69 (Irrelevant: 3.6 vs. DMF10.167.4:22.3), NCI-H128 (4.79 vs 115.49), HTB 171(10.44 vs. 673.85), HTB 173 (4.04 vs 20.91), HTB 175 (6.18 vs 730.46), DMS79 (8.38 vs 31.65), HTB 180 (6.21 vs 39.98), NCI-H187 (7.37 vs 374.5) and SHP-77 (5.69 vs 140.1). These data indicate that the DMF10.167.4 mAb recognizes monosialo-GM2 on SCLC cells and suggest that the mAb could be used for the therapeutic treatment of small cell lung cancer.

Example 11

DMF10.167.4 mAb Suppresses Human Melanoma Tumor Formation In Vivo

To determine if the anti-monosialo-GM2 mAb would suppress tumor formation (prophylactic model) in mice, we performed tumor model studies in vivo using the CHL-1 melanoma cell line. Fifteen female SCID mice were injected subcutaneously with $5 \times 10^6$ CHL-1 cells, and then separated into 3 groups of 5 animals. One group of five mice was untreated, one group received 100 µg of the hamster DMF10.167.4 anti-monosialo-GM2 mAb intravenously, and one group received 100 µg of an irrelevant hamster IgG i.v. at day 0 (time of tumor cell injection). On day 4, the mAb groups received an additional intravenous injection of the indicated antibodies. Tumor size was measured by caliper for 45 days, using the formula (length×width) to measure the tumor area. All five of the animals that received no treatment or received irrelevant hamster IgG developed easily detectable tumors by day 8 (mean tumor area=60 mm$^2$) which continued to expand throughout the course of the study, leading to their sacrifice at day 21 (mean tumor area=130 mm$^2$). Mice that had received hamster DMF10.167.4 mAb showed greater than 3-fold repression in tumor size (mean tumor area=40 mm$^2$) at day 21, and continued to show repressed growth, for at 45 days, the mean tumor area was 100 mm$^2$, which was still smaller than controls at day 21. These data demonstrate the potent anti-tumor formation activity in vivo of the DMF10.167.4 hamster anti-monosialo-GM2 mAb.

Example 12

Reactivity of Human Myeloma Cells with DMF 10.167.4 Antibody

The reactivity of human myeloma cells with the antibody DMF 10.167.4 was evaluated by indirect immunofluorescence and flow cytometry. Human myeloma cell lines were incubated with DMF.10.167.4 antibody or control hamster Ig on ice for 30-45 minutes. The cells were then washed and incubated with FITC-labeled anti-hamster Ig on ice for 30-45 minutes. The cells were subsequently washed and fixed with paraformaldehyde (1%×10'). The binding of fluorescent antibody was quantified with a flow cytometer.

In total, 6 myeloma cells lines were analyzed. As demonstrated by the increase in mean fluorescent intensity (MFI) values of the DMF10.167.4 mAb compared to irrelevant hamster IgG, which is a measurement of the relative binding ability of the mAb, the DMF10.167.4 mAb was shown to recognize and bind to monosialo-GM2 on the surface of myeloma cells lines, including MM-1S (irrelevant hamster IgG MFI~4 vs. DMF10.167.4 MFI~40) RPMI-8226 (~4 vs. ~25) and LP-1 (~4 vs. ~80). Two additional lines, OCI-My5 and EJM, both demonstrated weak binding (~3 vs. ~7) and one line, MM-1R was shown not to express monosialo-GM2 as it demonstrated no detectable binding.

The ability of the DMF10.167.4 mAb to inhibit the proliferation of myeloma cells in vitro was also tested. MM-1S cells were plated into a 96 well plate in triplicate in a final volume of 200 ul media. The cells were allowed to adhere for 4 hours, then 2.5-10 ug/ml of DMF10.167.4 mAb or control hamster IgG was added to the wells. Cells were grown for three days, after which time 25 uCi of $^3$H-thymidine was added per well. Following a four hour incubation, cells were lysed and then subjected to counting on a beta-counter to determine relative levels of $^3$H incorporation. The DMF10.167.4 mAb was shown to inhibit the proliferation of the MM-1S in a dose-dependent manner, as no treatment of cells yielded a CPM of 23,758, hamster IgG treatment of 2.5 ug/ml, 5 ug/ml, 10 ug/ml, and 20 ug/ml yielded 22,407, 21334, 16893, and 10818 CPM, respectively, whereas DMF10.167.4 treatment of 2.5 ug/ml, 5 ug/ml, 10 ug/ml, and 20 ug/ml yielded 7414, 2038, 984, and 544 CPM, respectively. Based on the same methods, similar results were observed for RPMI cells: no treatment of cells yielded a CPM of 2543, hamster IgG treatment of 2.5 ug/ml, 5 ug/ml, 10 ug/ml, and 20 ug/ml yielded 9343, 8036, 9748, and 5296 CPM, respectively, whereas DMF10.167.4 treatment of 2.5 ug/ml, 5 ug/ml, 10 ug/ml, and 20 ug/ml yielded 2626, 1269, 424, and 154 CPM, respectively. Collectively, these data demonstrate that DMF10.167.4 binds to GM2 expressed on myeloma cells and can block the proliferation of said myeloma cells, indicating that these tumors are a suitable target for DMF10.167.4 mAb immunotherapy.

Example 13

Generation of an Anti-Monosialo-GM2 Hamster-Human Chimeric Monoclonal Antibody

An anti-GM2 chimeric monoclonal antibody (ChGM2 mAb) was constructed with the variable regions of a hamster mAb and the constant regions of a human mAb. The light chain variable region of the ChGM2 mAb has the amino acid sequence of the light chain variable region of DMF10.167.4 SEQ ID NO: 23; and the heavy chain variable region of the ChGM2 mAb has the amino acid sequence of the heavy chain variable region of DMF10.167.4 of SEQ ID NO: 24. The constant region of the ChGM2 mAb is from a human IgG 1 isotype determined to have significant homology to the constant region of the anti-monosialo-GM2 hamster antibodies. The ChGM2 mAb has the light chain nucleotide sequence of SEQ ID NO: 7 and a heavy chain nucleotide sequence of SEQ ID NO: 8. Additionally, a chimeric antibody of the present invention may have the variable regions of the DMF10.62.3 monoclonal antibody.

The chimeric anti-monosialo-GM2 monoclonal antibody (mAb) was generated by fusing the hamster anti-monosialo-GM2 DMF10.167.4 mAb variable region domains to human IgG1 and kappa constant region domains. Multiple allotype (and isotype) constant regions could be used including f, a, z and combinations thereof for the heavy chain and 1, 2, 3, and combinations thereof for the light chain. Litwin, S. D. Immunol Sel. (1989) 43:203-236.

For chimeric generation, the DMF10.167.4 heavy (H) chain cDNA template) was PCR amplified using a 5' sense oligo (GTCGGCCGGAAGGGCCTTGGCCCAGGTCCAGCTGCAGCAGTCTG) SEQ ID NO: 4 and a 3' antisense oligo (ATGCTGGGCCCTTGGTGGAGGCTGAGGAGACAGTGACTTGGGTCCCTTGACC) SEQ ID NO: 3, restriction endonuclease digested with SfiI and ApaI and subcloned into an expression vector containing the human IgG1 constant region domains. Likewise, the DMF10.167.4 light (L) chain cDNA template was PCR amplified using a 5' sense oligo (ACTGGCCGGAAGGGCCTTGGCCGATATCGTGATGACACAGTCTCCA) SEQ ID NO: 2 and a 3' anti-sense oligo (AGACAGATGGCGCCGCCACGGTCCGTTTGATTTTCAGCTTGGTGCC) SEQ ID NO: 1, restriction endonuclease digested with SfiI and KasI and subcloned into an expression vector containing the human kappa constant region domain. These H and L chain expression constructs whose ORFs are defined by SEQ ID NOS: 7, 8, 21, 22 were transfected into CHO-K1 (ATCC No. CCL-61) cells to produce a chimeric anti-monosialo-GM2 mAb that was subsequently purified by protein A column chromatography.

The data presented herein demonstrate that the chimeric anti-monosialo-GM2 mAb with a hamster variable regions of the DMF10.167.4 mAb and a human $\gamma_1/\kappa$ constant regions retains biological properties of the DMF10.167.4 mAb. More specifically, the chimeric mAb retains the capacity to (1) bind to tumor cells displaying monosialo-GM2 on their cell surfaces and (2) to induce apoptosis in the tumor cells to which the antibody specifically binds.

Example 14

Chimeric Anti-Monosialo-GM2 mAb Induces Apoptosis of Several Human Tumor Cell Lines In Vitro In vitro cell culture experiments revealed that the hamster DMF10.167.4 mAb induced apoptosis in several human tumor lines as measured by annexin binding, including the Jurkat T cell leukemia line, the CHL-1 melanoma line and the HTB 175 SCLC line. Because annexin specifically binds to phosphatidylserine, which flips from the internal surface of the plasma membrane to the external surface upon initiation of apoptosis, one can use flow cytometric detection of annexin binding to evaluate the induction of apoptosis.

To validate that the ChGM2 mAb retained the apoptotic-inducing activity in vitro, these same experiments were repeated using the ChGM2 mAb. Jurkat cells were maintained overnight in normal growth media with no treatment, or incubated with either irrelevant human IgG or the ChGM2 mAb. While nearly 93% of cells receiving no treatment or irrelevant human IgG were viable, incubation with the ChGM2 mAb reduced the population of live cells to 69% and increased the percentage of apoptotic cells to 27% compared to 3% for the no treatment or irrelevant IgG groups. All treatments yielded the same percentage of late apoptotic or necrotic cells.

Additional in vitro annexin binding assays were performed using the CHL-1 melanoma and HTB 175 small cell lung cancer cell lines. As with the Jurkat cell line, the ChGM2 mAb was able to induce apoptosis in these lines. In the CHL-1 line, the percentage of apoptotic cells increased from 10% and 18% for no treatment and irrelevant human IgG, respectively, to 44% for ChGM2 treated cells. Moreover, despite the relatively high levels of basal apoptosis in the HTB 175 cell line, treatment with the ChGM2 mAb led to an increase in the percentage of apoptotic cells compared to those receiving irrelevant IgG or no treatment (45% vs. 32%). Collectively, these data demonstrate that the chimerization process has not destroyed the apoptotic activity inherent to the hamster DMF10.167.4 mAb.

Example 15

Chimeric Anti-monosialo-GM2 Monoclonal Antibody Suppresses Human Melanoma Tumor Formation In Vivo To determine if the anti-monosialo-GM2 mAb would suppress tumor formation (prophylactic model) in mice, we performed tumor model studies in vivo using the CHL-1 melanoma cell line. CHL-1 cells, grown in DMEM and 10% DMEM and 10% FCS, were lifted from tissue culture flasks by cell dissociation solution, washed in 1×PBS, then resuspended in 1×PBS. Fifteen female SCID mice were injected sub-cutaneously with $5 \times 10^6$ CHL-1 cells, and then separated into 3 groups of 5 animals. One group of five mice was untreated, one group received 100 µg of the ChGM2 anti-monosialo-GM2 mAb intravenously, and one group received 100 µg of an irrelevant human IgG i.v. at day 0 (time of tumor cell injection). On days 4 and 8, the mAb groups received an additional intravenous injection of the indicated antibodies. Tumor size was measured by caliper for 45 days, using the formula (length×width) to measure the tumor area. All five of the animals that received no treatment or received irrelevant human IgG developed easily detectable tumors by day 8 (mean tumor area=55-60 mm$^2$) which continued to expand throughout the course of the study, leading to their sacrifice at day 21 (mean tumor area=120 mm$^2$). Mice that had received ChGM2 mAb showed greater than 6-fold repression in tumor size (mean tumor area=20 mm$^2$) at day 21, and continued to show repressed growth, for at 45 days, the mean tumor area was ~30 mm$^2$, which was still smaller than controls at day 21. These data demonstrate the potent anti-tumor formation activity in vivo of the ChGm2 anti-monosialo-GM2 mAb and its effectiveness in suppressing tumor cell growth in a prophylactic mouse tumor model system.

Example 16

Therapeutic Human Melanoma Tumor Suppression In Vivo by the DMF10. Hamster-Human Chimeric Anti-Monosialo-GM2 mAb The chimeric anti-monosialo-GM2 antibodies (ChGM2 mAb) of the present invention are effective in suppressing tumor cell growth in a therapeutic murine tumor model system employing the human melanoma cell-line CHL-1.

A xenograft tumor model using CHL-1 human melanoma cells implanted in SCID mice was established to test the efficacy of the anti-monosialo-GM2 monoclonal antibody DMF10.167.4. Approximately $5 \times 10^6$ CHL-1 tumor cells were implanted, subcutaneously, in SCID mice. Seven days later, when tumors of approximately 20 square millimeters were established, mice with tumors were randomly segregated into two groups of six animals. The control group received 100 µg per day of human IgG antibody on days 7, 11, 14, 18 and 22. The second group received 100 µg per day of chimeric anti-monosialo-GM2 antibody also on days 7, 11, 14, 18 and 22. Tumor size was measured for 27 days, using the formula length×width to measure tumor area. All of the six animals that received irrelevant human IgG had tumors of mean area=100 mm² at 26 days, while the 6 mice that received ChGM2 mAb showed at least a five times reduction in tumor size (mean tumor area=20 mm²) at 26 days. These results demonstrate the suppressive effect of the ChGM2 mAb in melanoma tumors.

Example 17

In vivo Repression of Human SCLC Tumor Growth with Chimeric Anti-monosialo-GM2 Antibody To extend the functional analysis of the ChGM2 mAb in vivo, additional SCID tumor model studies were performed using HTB 175 SCLC cells to determine if this mAb could suppress the progression of established SCLC tumors. Twenty female SCID mice were injected subcutaneously with $4 \times 10^6$ HTB 175 SCLC cells and tumors were allowed to establish for 15 days. The mean tumor area for the HTB 175 cells was 38 mm², approximately twice as large as the CHL-1 tumors in the previous study. At this time, the mice were randomized into two groups of 9 mice based on tumor size, and one group received 100 µg of the ChGM2 mAb and one group received 100 µg of irrelevant human IgG intravenously. On days 19 and 22, each group received only 80 µg of their respective dose of ChGM2 mAb, and it was delivered i.p. due to difficulties with i.v delivery during this experiment. Tumor size (area) was measured for 26 days. HTB 175 tumor growth continued in all nine of the animals that received irrelevant human IgG treatment, whereas the mice that had received ChGM2 mAb demonstrated a reduction in the progression of tumor growth. Collectively, these in vivo tumor model studies demonstrate the potential therapeutic efficacy of this ChGM2 mAb for the treatment of melanoma and SCLC tumors.

Example 18

In vivo Apoptosis with Chimeric Anti-Monosialo-GM2 Antibody

To determine if ADCC (antibody-dependent cellular cytotoxicity) plays a role in the ChGM2 mAbs ability to inhibit CHL-1 tumor formation in vivo, a tumor model study was carried out comparing the activity of the chimeric anti-monosialo-GM2 antibodies in SCID mice to SCID/beige mice. Due to the beige mutation, these mice have been reported to be deficient in macrophages and possess selectively impaired natural killer cells, leading to their inability to carry out ADCC. Two groups of five SCID and two groups of five SCID/beige mice were injected with $5 \times 10^6$ CHL-1 cells subcutaneously on day 0. The mice were then injected i.v. with 100 µg/injection of human irrelevant IgG or ChGM2 mAb on days 0, 3, 7, and 13. Tumor size (area) was measured for 35 days. Tumor formation was completely suppressed in 4 out of 5 mice in both the SCID and SCID/beige groups after ChGM2 treatment (tumor area=0 mm²), whereas all 5 SCID mice (tumor area>120 mm² each) and 4 of 5 SCID/beige (tumor area>100 mm²) formed tumors when injected with irrelevant human IgG. These results demonstrate that the ChGM2 is able to block tumor formation without requiring cell-mediated immune effector cells, suggesting that the apoptotic ability of this antibody alone is responsible for the lack of tumor formation, and possibly tumor progression, in vivo, again supporting the use of the mAb as a naked, non-conjugated form for the therapeutic treatment of monosialo-GM2-expressing myeloma tumors.

Example 19

Human Myeloma Cell-Surface Binding by ChGM2mAb

To determine if monosialo-GM2 is expressed on the surface of myeloma cells and recognized by the ChGM2 mAb, $1 \times 10^6$ cells were incubated with 10 µg/ml irrelevant human IgG or ChGM2 mAb on ice, then washed 3 times with staining buffer (PBS+1% BSA+Azide). Cells were then incubated with FITC-conjugated anti-human IgG on ice, and then washed 3 times with staining buffer. Cells were resuspended in staining buffer containing propidium iodide, a vital stain that distinguishes permeable cells from viable cells, then analyzed by flow cytometry. As demonstrated by the increase in the mean fluorescent intensity (MFI) values of the ChGM2 mAb compared to irrelevant human IgG, which is a measurement of the relative binding ability, the ChGM2 mAb was shown to recognize and bind to monosialo-GM2 on the surface of several myeloma cell lines, including DP-6 (Irrelevant: 6.26 vs. ChGM2:24.73), OPM-2 (2.98 vs. 86.27), U266 (1.96 vs. 165.19), and RPMI-8226 (4.94 vs. 12.38). The ChGM2 bound weakly to the NCI-H929 myeloma line (20 µg/ml; 8.34 vs. 14.34). These data indicate that the ChGM2 mAb recognizes monosialo-GM2 on a number of myeloma cell lines and could be used for the therapeutic treatment of multiple myeloma.

Example 20

Apoptosis of Human Myeloma Cells by ChGM2mAb mAb Treatment

To demonstrate the apoptotic potential of the ChGM2 mAb on myeloma cells, $2 \times 10^5$ U-266 cells were plated and incubated overnight with 20 µg/ml of the anti-ChGM2 mAb or irrelevant human IgG, then assayed for annexin positivity by incubating the cells with an annexin V-Alexa488 conjugate (Molecular Probes). Cells were subjected to flow cytometric analysis to determine the amount of annexin positivity as a measure of ChGM2 mAb-induced apoptotic activity. The irrelevant human IgG revealed a background of 20.5% apoptosis, whereas the ChGM2 mAb was responsible for inducing 44% of the cells to undergo apoptosis, a greater than 2-fold increase. These data indicate that the chimeric anti-monosialo-GM2 mAb could be used in a naked, non-conjugated form as a therapeutic treatment of monosialo-GM2- expressing myeloma tumors due to the apoptotic-inducing and subsequent tumor killing ability of the mAb.

Example 21

Antibody-Dependent Cellular Cytotoxicity of ChGM2 Antibody

The ability of an antibody to mediate antibody-dependent cellular cytotoxicity (ADCC) is a property that can be of importance in therapeutic methods. An experiment was conducted to test the ADCC mediating potential in vitro of the chimeric anti-monosialo-GM2 antibodies of the present invention. Peripheral blood mononuclear cells (PBMCs), antibodies, and CHL-1 cells were incubated together in various combinations and then assayed for the ability of the PBMCs to kill CHL-1 cells in the presence of the anti-monosialo-GM2 antibody. The chimeric anti-monsialo-GM2 antibody was determined to induce cell-mediated killing in vitro.

PBMCs were isolated from heparinized whole blood using Histopaque-1077 (Sigma). The isolated PBMCs were washed three times in PBS and resuspended at $5.0 \times 10^6$ cells/100 µl in phenol red free RPMI (Invitrogen) containing 1% BSA. CHL-1 cells were lifted off the dish in Cell Dissociation Solution (Sigma), washed in PBS, and resuspended to $1.0 \times 10^4$ cells/50 µl in phenol red free RPMI containing 1% BSA. Human Chimeric anti-monosialo-GM2 antibody and Human IgG control antibody were distributed into three 4x stocks each of 4 µg/ml, 0.4 µg/ml, and 0.04 µl in phenol red free RPMI containing 1% BSA.

Samples for the experiment were prepared in quadruplicate with the following: 100 µl PBMCs, 50 µl CHL-1, and 50 µl of antibody (sample subsets included the 3 different concentrations of antibody using both antibody types, an additional set of controls following the conditions outlined above but without PBMCs was done to control for apoptosis induced by the anti-monosialo-GM2 antibody alone). Additionally, a sample set containing just PBMCs and CHL-1 cells was included as a background control (BC), and sonicated CHL-1 cells with viable PBMC's was included as the "maximum release" control, or high control (HC). In samples where one of the three components was missing, RPMI+1% BSA was substituted to maintain equal volumes in all samples of 200 µl. The samples were then incubated at 37° C. for 4 hours in a 7% $CO_2$ atmosphere.

Killing of CHL-1 cells by PBMCs was assayed by screening for the presence of lactate deyhydrogenase (LDH) in the supernatant of each sample (as a cell dies it's membrane becomes permeable, thus allowing LDH to leak into the medium) using the LDH Cytotoxicity Detection Kit (Takara Shuzo Co., LTD.). Briefly, 250 µl of solution A was mixed with 11.25 ml solution B immediately before use and 100 µl of this working stock (A+B) was added to 100 µl of each sample supernatant (note: samples were spun for 2 minutes at 1800 RPM and 100 µl of supernatant was transferred to a new 96 well plate prior to the addition of LDH substrate). Samples were developed in the dark for 15 minutes and then read on a 96 well plate spectrophotometer at 490 nm. Sample absorbance (A) measurements were converted to percent killing by the following equation: percent killing=$[(A-BC)/(HC-BC)]*100$.

The percent of the CHL-1 cells killed in the presence of the chimeric anti-monosialo-GM2 was high and dose dependent. In the samples with 1 µg/ml of the chimeric anti-monosialo-GM2 antibody and in the presence of PBMCs, about 83% killing was observed. In the samples with 0.1 µg/ml of the chimeric anti-monosialo-GM2 antibody and in the presence of PBMCs, about 66% killing was observed. In the samples with 0.01 µg/ml of the chimeric anti-monosialo-GM2 antibody and in the presence of PBMCs, about 21% killing was observed. In contrast the human IgG control antibodies demonstrated low levels of PBMC killing possibly due to nonspecific binding of the control antibodies to the CHL-1 cells. About 15%, 10%, and 8% killing was observed with the control antibodies in the presence of PBMCs. Additionally, no significant killing was observed in the samples without PBMCs and with either the chimeric anti-monosialo-GM2 antibodies or the control antibodies. It should be noted that the chimeric anti-monosialo-GM2 has shown apoptotic properties independent of PBMCs, but due to the short duration of these assays this apoptotic ability would not be evident. These data demonstrate that the chimeric anti-monosialo-GM2 antibodies of the present invention are able to mediate antibody-dependent cellular cytotoxicity.

Deposit Statement

The hybridoma cell line producing the monoclonal antibody DMF10.62.3, was received by the American Type Culture Collection (ATCC), 10801 University Boulevard, Manassas, Va., on Jul. 20, 1999, and the hybridoma cell lines producing the monoclonal antibodies DMF10.167.4 and DMF10.34.36 were received by the American Type Culture Collection (ATCC), 10801 University Boulevard, Manassas, Va., on Jul. 22, 1999. The hybridomas have been deposited under conditions that assure that access to the hybridomas will be available during the pendency of the patent application disclosing them to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action. Further, the subject culture deposits will be stored and made available to the public in accord with the provisions of the Budapest Treaty for the Deposit of Microorganism, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures plus five years after the last request for a sample from the deposit. The depositor acknowledges the duty to replace the deposit should the depository be unable to furnish a sample when requested, due to the condition of the deposits. All restrictions on the availability to the public of the subject culture deposit will be irrevocably removed upon the granting of a patent disclosing them.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inhibiting proliferation of a myeloma tumor cell expressing a GM2 ganglioside antigen, the method comprising contacting the myeloma tumor cell with an unconjugated anti-GM2 IgG antibody, wherein the unconjugated anti-GM2 IgG antibody i.) specifically binds to the GM2 ganglioside and ii.) is capable of inhibiting proliferation of the myeloma tumor cell in the absence of antibody-dependent cellular cytotoxicity (ADCC), such that proliferation of the myeloma tumor cell expressing the GM2 ganglioside is inhibited.

2. A method of inhibiting proliferation of a human melanoma tumor cell expressing a ganglioside antigen, the method comprising contacting the human melanoma cell with an unconjugated anti-GM2 IgG antibody, wherein the unconjugated anti-GM2 IgG antibody i.) specifically binds to the GM2 ganglioside and ii.) is capable of inhibiting proliferation of the melanoma tumor cell in the absence of antibody-dependent cellular cytotoxicity (ADCC), such that proliferation of the human melanoma tumor cell expressing the GM2 ganglioside is inhibited.

3. The method of any one of claim 1 or 2, wherein the antibody is selected from the group consisting of a chimeric antibody, a humanized antibody, a human antibody, and a primatized antibody.

4. The method of any one of claim 1 or 2, wherein the antibody is selected from the group consisting of monoclonal antibody DMF10.167.4 produced by a hybridoma cell line deposited under ATCC No. PTA-405, monoclonal antibody DMF10.62.3 produced by a hybridoma cell line deposited under ATCC No. PTA-377, a chimeric antibody having a variable region of the DMF10.167.4 monoclonal antibody produced by a hybridoma cell line deposited under ATCC No. PTA-405, a chimeric antibody having a variable region of the DMF10.62.3 monoclonal antibody produced by a hybridoma cell line deposited under ATCC No. PTA-377, and a humanized antibody having all complementarity determining regions of the DMF10.167.4 monoclonal antibody produced by a hybridoma cell line deposited under ATCC No. PTA-405.

5. The method of claim 4, wherein the antibody is a chimeric antibody having a light chain amino acid sequence of SEQ ID NO:21 and a heavy chain amino acid sequence of SEQ ID NO:22.

6. The method of claim 3, wherein the antibody comprises a modified version of an amino acid shown in SEQ ID NO: 21, the modification comprising substitution of isoleucine at linear position 52 of the sequence of the light chain variable region of SEQ ID NO:21 with valine, and further comprises a modified version of an amino acid shown in SEQ ID NO: 22, the modification comprising substitution of threonine at linear position 78 of the sequence of the heavy chain variable region of SEQ ID NO:22 with lysine.

7. The method of any one of claim 1 or 2, wherein the antibody is a purified chimeric antibody, or antigen-binding fragment thereof, wherein the antibody or fragment thereof comprises a light chain having the amino acid sequence of SEQ ID NO:21 and a heavy chain having the amino acid sequence of SEQ ID NO:22.

8. The method of claim 7, wherein the antibody is effective at inhibiting cell proliferation of a tumor cell to which the antibody specifically binds.

9. The method of claim 7, wherein the antibody is effective at inducing apoptosis in a tumor cell to which the antibody specifically binds.

10. The method of claim 7, wherein the antibody induces apoptosis in a monolayer, or a single-cell suspension of the tumor cells, or both.

11. The method of any one of claim 1 or 2, wherein the antibody comprises a modification to an amino acid shown in SEQ ID NO: 21, the modification comprising substitution of isoleucine at linear position 52 of the sequence of the light chain of SEQ ID NO:21 of the antibody with valine.

12. The method of any one of claim 1 or 2, wherein the antibody comprises a modified version of an amino acid shown in SEQ ID NO: 22, the modification comprising substitution of threonine at linear position 78 of the heavy chain of SEQ ID NO:22 of the antibody with lysine.

13. The method of any one of claim 1 or 2, wherein the antibody is a purified antibody, or antigen-binding fragment thereof, wherein the antibody comprises complementarity determing regions (CDRs) with amino acid sequences shown in SEQ ID NO:13, SEQ ID NO:14, SEQ ID NO:15, SEQ ID NO:16, SEQ ID NO:17, and SEQ ID NO:18.

14. The method of claim 13, wherein the antibody is effective in inducing apoptosis in a tumor cell to which the antibody specifically binds.

15. The method of claim 13, wherein the antibody induces apoptosis in a monolayer, a single-cell suspension of the tumor cells, or both.

16. The method of any one of claim 1 or 2, wherein the antibody comprises an amino acid sequence shown in SEQ ID NO:19 and SEQ ID NO:20.

17. The method of any one of claim 1 or 2, wherein the antibody is a purified monoclonal antibody, or antigen-binding fragment thereof, wherein the monoclonal antibody comprises the amino acid sequence shown in SEQ ID NO:19 and SEQ ID NO:20, or an antigen-binding fragment thereof.

18. The method of any one of claim 1 or 2, wherein the antibody is a purified monoclonal antibody, or antigen-binding fragment thereof, wherein the monoclonal antibody comprises the amino acid sequence shown in SEQ ID NO:23 and SEQ ID NO:24, or an antigen-binding fragment thereof.

19. The method of any one of claim 1 or 2, wherein the antibody is a purified monoclonal antibody, or antigen-binding fragment thereof, wherein the monoclonal antibody comprises the amino acid sequence shown in SEQ ID NO:25 and SEQ ID NO:26, or an antigen-binding fragment thereof.

20. The method of any one of claim 1 or 2, wherein the antibody comprises a polypeptide comprising the amino acid sequence shown in SEQ ID NO:23 and SEQ ID NO:24.

21. The method of any one of claim 1 or 2, wherein the antibody comprises a polypeptide comprising the amino acid sequence shown in SEQ ID NO:25 and SEQ ID NO:26.

22. A method of inhibiting proliferation of a small cell lung cancer (sclc) tumor cell expressing a ganglioside antigen, the method comprising contacting the sclc cell with an antibody, wherein the antibody specifically binds to the ganglioside, such that proliferation of the sclc tumor cell expressing the ganglioside is inhibited, wherein the antibody is selected from the group consisting of monoclonal antibody DMF10.167.4 produced by a hybridoma cell line deposited under ATCC No. PTA-405, monoclonal antibody DMF10.62.3 produced by a hybridoma cell line deposited under ATCC No. PTA-377, a chimeric antibody having a variable region of the DMF10.167.4 monoclonal antibody produced by a hybridoma cell line deposited under ATCC No. PTA-405, a chimeric antibody having a variable region of the DMF10.62.3 monoclonal antibody produced by a hybridoma cell line deposited under ATCC No. PTA-377, and a humanized antibody having all complementarity determining regions of the DMF10.167.4 monoclonal antibody produced by a hybridoma cell line deposited under ATCC No. PTA-405.

23. The method of claim 22, wherein the antibody is a chimeric antibody having a light chain amino acid sequence of SEQ ID NO:21 and a heavy chain amino acid sequence of SEQ ID NO:22.

24. The method of claim 23, wherein the antibody comprises a modification to an amino acid shown in SEQ ID NO: 21, the modification comprising substitution of isoleucine at linear position 52 of the sequence of the light chain variable region of SEQ ID NO:21 with valine, and further comprises a modification to an amino acid shown in SEQ ID NO: 22, the modification comprising substitution of threonine at linear position 78 of the sequence of the heavy chain variable region of SEQ ID NO:22 with lysine.

25. The method of claim 22, wherein the antibody is a purified chimeric antibody, or antigen-binding fragment thereof, wherein the antibody or fragment thereof comprises a light chain having the amino acid sequence of SEQ ID NO:21 and a heavy chain having the amino acid sequence of SEQ ID NO:22.

26. The method of claim 25, wherein the antibody is effective in inhibiting cell proliferation of a tumor cell to which the antibody specifically binds.

27. The method of claim 25, wherein the antibody is effective in inducing apoptosis in a tumor cell to which the antibody specifically binds.

28. The method of claim 25, wherein the antibody induces apoptosis in a monolayer, or a single-cell suspension of the tumor cells, or both.

29. The method of claim 25, wherein the antibody comprises a modification to an amino acid shown in SEQ ID NO: 21, the modification comprising substitution of isoleucine at linear position 52 of the sequence of the light chain of SEQ ID NO:21 of the antibody with valine.

30. The method of claim 25, wherein the antibody comprises a modification to an amino acid shown in SEQ ID NO: 22, the modification comprising substitution of threonine at linear position 78 of the heavy chain of SEQ ID NO:22 of the antibody with lysine.

31. The method of claim 25, wherein the antibody comprises a modification to an amino acid shown in SEQ ID NO: 21, the modification comprising substitution of isoleucine at linear position 52 of the sequence of the light chain of SEQ ID NO:21 of the antibody with valine and the antibody further comprises a modification to an amino acid shown in SEQ ID NO: 22, the modification comprising substitution of threonine at linear position 78 of the heavy chain of SEQ ID NO:22 of the antibody with lysine.

32. The method of claim 22, wherein the antibody is a purified antibody, or antigen-binding fragment thereof, wherein the antibody comprises complementarity determining regions (CDRs) with amino acid sequences shown in SEQ ID NO:13, SEQ ID NO:14, SEQ ID NO:15, SEQ ID NO:16, SEQ ID NO:17, and SEQ ID NO:18.

33. The method of either of claim 13 or 32, wherein the antibody further comprises a human constant or framework region.

34. The method of claim 33, wherein the antibody further comprises at least one conservative amino acid substitution.

35. The method of claim 34, wherein the at least one conservative amino acid substitution is within the human constant or framework region.

36. The method of claim 32, wherein the antibody is effective in inducing apoptosis in a tumor cell to which the antibody specifically binds.

37. The method of claim 32, wherein the antibody induces apoptosis in a monolayer, a single-cell suspension of the tumor cells, or both.

38. The method of claim 22, wherein the antibody comprises an amino acid sequence shown in SEQ ID NO:19 and SEQ ID NO:20.

39. The method of claim 22, wherein the antibody is a purified monoclonal antibody, or antigen-binding fragment thereof, wherein the monoclonal antibody comprises the amino acid sequence shown in SEQ ID NO:19 and SEQ ID NO:20, or an antigen-binding fragment thereof.

40. The method of claim 22, wherein the antibody is a purified monoclonal antibody, or antigen-binding fragment thereof, wherein the monoclonal antibody comprises the amino acid sequence shown in SEQ ID NO:23 and SEQ ID NO:24, or an antigen-binding fragment thereof.

41. The method of claim 22, wherein the antibody is a purified monoclonal antibody, or antigen-binding fragment thereof, wherein the monoclonal antibody comprises the amino acid sequence shown in SEQ ID NO:25 and SEQ ID NO:26, or an antigen-binding fragment thereof.

42. The method of claim 22, wherein the antibody comprises a polypeptide comprising the amino acid sequence shown in SEQ ID NO:23 and SEQ ID NO:24.

43. The method of claim 22, wherein the antibody comprises a polypeptide comprising the amino acid sequence shown in SEQ ID NO:25 and SEQ ID NO:26.

44. The method of claim 22, wherein the antibody i) specifically binds to a tumor cell expressing the GM2 ganglioside and ii) is capable of inhibiting proliferation of the tumor cell in the absence of antibody-dependent cellular cytotoxicity (ADCC).

45. The method of any one of claim 1, 2, or 22, wherein the proliferation of the tumor cell expressing the GM2 ganglioside is inhibited in vivo.

46. A method of inhibiting proliferation of a myeloma tumor cell expressing a GM2 ganglioside antigen, the method comprising contacting the myeloma tumor cell with an unconjugated anti-GM2 IgG antibody, wherein the unconjugated anti-GM2 IgG antibody i.) specifically binds to the GM2 ganglioside and ii.) is capable of inhibiting proliferation of the myeloma tumor cell in an in vitro assay in the absence of cell-mediated immune effector cells, such that proliferation of the myeloma tumor cell expressing the GM2 ganglioside is inhibited.

47. A method of inhibiting proliferation of a human melanoma tumor cell expressing a ganglioside antigen, the method comprising contacting the human melanoma cell with an unconjugated anti-GM2 IgG antibody, wherein the unconjugated anti-GM2 IgG antibody i.) specifically binds to the GM2 ganglioside and ii.) is capable of inhibiting proliferation of the melanoma tumor cell in an in vitro assay in the absence of cell-mediated immune effector cells, such that proliferation of the human melanoma tumor cell expressing the GM2 ganglioside is inhibited.

48. A method of inhibiting proliferation of a human tumor cell expressing a ganglioside antigen, the method comprising contacting the human tumor cell with an unconjugated anti-GM2 IgG antibody, wherein the unconjugated anti-GM2 IgG antibody i.) specifically binds to the GM2 ganglioside and ii.) is capable of inhibiting proliferation of the human tumor cell in an in vitro assay in the absence of antibody-dependent cellular cytotoxicity (ADCC), such that proliferation of the human tumor cell expressing the GM2 ganglioside is inhibited.

49. The method of claim 48, wherein the proliferation of the tumor cell expressing the GM2 ganglioside is inhibited in vivo.

50. A method of inhibiting proliferation of a tumor cell expressing a GM2 ganglioside antigen, the method comprising i) selecting an IgG antibody based on its ability to specifically bind to GM2 and to inhibit proliferation of a tumor cell in the absence of antibody-dependent cellular cytotoxicity (ADCC), ii) contacting the tumor cell with the antibody, such that proliferation of the tumor cell expressing the GM2 ganglioside is inhibited, wherein the tumor cell is selected from the group consisting of: a myeloma tumor cell, a melanoma tumor cell, and a small cell lung cancer tumor cell.

\* \* \* \* \*

SEQUENCE LISTING

<160> NUMBER OF SEQ ID NOS: 26

<210> SEQ ID NO 1
<211> LENGTH: 46
<212> TYPE: DNA
<213> ORGANISM: Artificial
<220> FEATURE:
<223> OTHER INFORMATION: Synthetic Oligonucleotide

<400> SEQUENCE: 1
agacagatgg cgccgccacg gtccgtttga ttttcagctt ggtgcc         46

<210> SEQ ID NO 2
<211> LENGTH: 46
<212> TYPE: DNA
<213> ORGANISM: Artificial
<220> FEATURE:
<223> OTHER INFORMATION: Synthetic Oligonucleotide

<400> SEQUENCE: 2
actggccgga agggccttgg ccgatatcgt gatgacacag tctcca         46

<210> SEQ ID NO 3
<211> LENGTH: 52
<212> TYPE: DNA
<213> ORGANISM: Artificial
<220> FEATURE:
<223> OTHER INFORMATION: Synthetic Oligonucleotide

<400> SEQUENCE: 3
atgctgggcc cttggtggag gctgaggaga cagtgacttg ggtcccttga cc    52

<210> SEQ ID NO 4
<211> LENGTH: 44
<212> TYPE: DNA
<213> ORGANISM: Artificial
<220> FEATURE:
<223> OTHER INFORMATION: Synthetic Oligonucleotide

<400> SEQUENCE: 4
gtcggccgga agggccttgg cccaggtcca gctgcagcag tctg         44

<210> SEQ ID NO 5
<211> LENGTH: 336
<212> TYPE: DNA
<213> ORGANISM: Cricetulus migratorius

<400> SEQUENCE: 5
gacatcgtga tgacacagtc tccatcttcc ttggctgtgt cagcaggaga cacggtcacc    60
atcaactgca ggtccagtca gagtcttttc tctggaaatt ataactattt ggcttggtac   120
cagcagaaaa cagggcagac tcctaaatta ctggtctctt acgcatccac tcggcacact   180
ggtgtccctg atcgcttcgt gggcagtgga tctgggacag atttcattct aaccatctac   240
aatttccaga ctgaagatct gggagattac tattgccagc agcattacag ttctcctcgg   300
acgtttggac ctggcaccaa gctgaaaatc aaacgg                              336

<210> SEQ ID NO 6
<211> LENGTH: 357
<212> TYPE: DNA
<213> ORGANISM: Cricetulus migratorius

<400> SEQUENCE: 6

-continued

```
caggtccagc tgcagcagtc tggggctgag ctggtgaaac ccggagcctc agtgaggctg     60
tcctgcaaga cttcaggcta cacgtttacc actcactatg tgagctgggt gaaacagaag    120
cctggacagg gactggagtg gattggatgg atttttggtg gaagtgctag aactaattat    180
aatcagaaat tccagggcaa ggccacactg actgtagaca catcctccag caaggcctac    240
atggatctca gaagcctgac atctgatgac tctgcagtct atttctgtgt aagacaagta    300
gggtgggacg atgctctgga tttctggggt caagggaccc aagtcactgt ctcctca       357
```

<210> SEQ ID NO 7
<211> LENGTH: 657
<212> TYPE: DNA
<213> ORGANISM: Artificial
<220> FEATURE:
<223> OTHER INFORMATION: Chimeric Cricetulus migratorius and Human

<400> SEQUENCE: 7

```
gatatcgtga tgacacagtc tccatcttcc ttggctgtgt cagcaggaga cacggtcacc     60
atcaactgca ggtccagtca gagtcttttc tctggaaact ataactattt ggcttggtac    120
cagcagaaaa cagggcagac tcctaaatta ctgatctctt acgcatccac tcggcacact    180
ggtgtccctg atcgcttcgt gggcagtgga tctgggacag atttcattct aaccatctac    240
aatttccaga ctgaagatct gggagattac tattgccagc agcattacag ttctcctcgg    300
acgtttggac ctggcaccaa gctgaaaatc aaacggaccg tggcggcgcc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca aagtctacgc ctgcgaagtc    600
acccatcagg gcctgtctag ccccgtcaca aagagcttca accgcggaga gtgttaa       657
```
<210> SEQ ID NO 8
<211> LENGTH: 1353
<212> TYPE: DNA
<213> ORGANISM: Artificial
<220> FEATURE:
<223> OTHER INFORMATION: Chimeric Cricetulus migratorius and Human

<400> SEQUENCE: 8

```
caggtccagc tgcagcagtc tggggctgag ctggtgaaac ccggagcctc agtgaggctg     60
tcctgcaaga cttcaggcta cacgtttacc actcactatg tgagctgggt gaagcagaag    120
cctggacagg gactggagtg gattggatgg atttttggtg gaagtgctag aactaattat    180
aatcagaaat tccagggcaa ggccacactg actgtagaca catcctccag cacggcctac    240
atggatctca gaagcctgac atctgatgac tctgcagtct atttctgtgt aagacaagta    300
gggtgggacg atgctctgga tttctggggt caagggaccc aagtcactgt ctcctcagcc    360
tccaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagagagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
```

```
gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggtg tacaccctgc ccccatcccg ggaggagatg     1080
accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctatagc aagctcaccg tggacaagag caggtggcag     1260
caggggaacg tcttctcatg ctccgtgatg catgaggctc tgcacaacca ctacacgcag     1320
aagagcctct ccctgtctcc gggtaaatga tga                                   1353

<210> SEQ ID NO 9
<211> LENGTH: 336
<212> TYPE: DNA
<213> ORGANISM: Cricetulus migratorius

<400> SEQUENCE: 9
gatatcgtga tgacacagtc tccatcttcc ttggctgtgt cagcaggaga cacggtcacc       60
atcaactgca ggtccagtca gagtcttttc tctggaaact ataacatttt ggcttggtac      120
cagcagaaaa cagggcagac tcctaaatta ctgatctctt acgcatccac tcggcacact      180
ggtgtccctg atcgcttcgt gggcagtgga tctgggacag atttcattct aaccatctac      240
aatttccaga ctgaagatct gggagattac tattgccagc agcattacag ttctcctcgg      300
acgtttggac ctggcaccaa gctgaaaatc aaacgg                                336

<210> SEQ ID NO 10
<211> LENGTH: 357
<212> TYPE: DNA
<213> ORGANISM: Cricetulus migratorius

<400> SEQUENCE: 10
caggtccagc tgcagcagtc tggggctgag ctggtgaaac ccggagcctc agtgaggctg       60
tcctgcaaga cttcaggcta cacgtttacc actcactatg tgagctgggt gaagcagaag      120
cctggacagg gactggagtg gattggatgg atttttggtg gaagtgctag aactaattat      180
aatcagaaat tccagggcaa ggccacactg actgtagaca catcctccag cacggcctac      240
atggatctca gaagcctgac atctgatgac tctgcagtct attttctgtgt aagacaagta      300 gggtgggacg atgctctgga tttctggggt caagggaccc aagtcactgt ctcctca         357

<210> SEQ ID NO 11
<211> LENGTH: 396
<212> TYPE: DNA
<213> ORGANISM: Cricetulus migratorius

<400> SEQUENCE: 11
atggagtcac acaatgaggt ccttgtgacc ctgctgctct gggtgtctgg tgcctgtgca       60
gatatcgtga tgacacagtc tccatcttcc ttggctgtgt cagcaggaga cacggtcacc      120
atcaactgca ggtccagtca gagtcttttc tctggaaact ataacatttt ggcttggtac      180
cagcagaaaa cagggcagac tcctaaatta ctgatctctt acgcatccac tcggcacact      240
ggtgtccctg atcgcttcgt gggcagtgga tctgggacag atttcattct aaccatctac      300
aatttccaga ctgaagatct gggagattac tattgccagc agcattacag ttctcctcgg      360
```

```
acgtttggac ctggcaccaa gctgaaaatc aaacgg                              396
```

<210> SEQ ID NO 12
<211> LENGTH: 414
<212> TYPE: DNA
<213> ORGANISM: Cricetulus migratorius

<400> SEQUENCE: 12

```
atgggatgga gctggatcat cctcttcctg gtgacagcag ctacaggtgt ccactcccag     60
gtccagctgc agcagtctgg ggctgagctg gtgaaacccg gagcctcagt gaggctgtcc   120
tgcaagactt caggctacac gtttaccact cactatgtga gctgggtgaa gcagaagcct   180
ggacagggac tggagtggat tggatggatt tttggtggaa gtgctagaac taattataat   240
cagaaattcc agggcaaggc cacactgact gtagacacat cctccagcac ggcctacatg   300
gatctcagaa gcctgacatc tgatgactct gcagtctatt tctgtgtaag acaagtaggg   360
tgggacgatg ctctggattt ctggggtcaa gggacccaag tcactgtctc ctca         414
```

<210> SEQ ID NO 13
<211> LENGTH: 9
<212> TYPE: PRT
<213> ORGANISM: Cricetulus migratorius

<400> SEQUENCE: 13

```
Gln Gln His Tyr Ser Ser Pro Arg Thr
1               5
```

<210> SEQ ID NO 14
<211> LENGTH: 7
<212> TYPE: PRT
<213> ORGANISM: Cricetulus migratorius

<400> SEQUENCE: 14

```
Tyr Ala Ser Thr Arg His Thr
1               5
```

<210> SEQ ID NO 15
<211> LENGTH: 15
<212> TYPE: PRT
<213> ORGANISM: Cricetulus migratorius

<400> SEQUENCE: 15

```
Arg Ser Ser Gln Ser Leu Phe Ser Gly Asn Tyr Asn Tyr Leu Ala
1               5                   10                  15
```

<210> SEQ ID NO 16
<211> LENGTH: 10
<212> TYPE: PRT
<213> ORGANISM: Cricetulus migratorius

<400> SEQUENCE: 16

```
Gln Val Gly Trp Asp Asp Ala Leu Asp Phe
1               5                   10
```

<210> SEQ ID NO 17
<211> LENGTH: 17
<212> TYPE: PRT
<213> ORGANISM: Cricetulus migratorius

<400> SEQUENCE: 17

```
Trp Ile Phe Gly Gly Ser Ala Arg Thr Asn Tyr Asn Gln Lys Phe Gln
1               5                   10                  15

Gly
```

-continued

<210> SEQ ID NO 18
<211> LENGTH: 5
<212> TYPE: PRT
<213> ORGANISM: Cricetulus migratorius

<400> SEQUENCE: 18

Thr His Tyr Val Ser
1               5

<210> SEQ ID NO 19
<211> LENGTH: 112
<212> TYPE: PRT
<213> ORGANISM: Cricetulus migratorius

<400> SEQUENCE: 19

Asp Ile Val Met Thr Gln Ser Pro Ser Ser Leu Ala Val Ser Ala Gly
1               5                   10                  15

Asp Thr Val Thr Ile Asn Cys Arg Ser Ser Gln Ser Leu Phe Ser Gly
            20                  25                  30

Asn Tyr Asn Tyr Leu Ala Trp Tyr Gln Gln Lys Thr Gly Gln Thr Pro
        35                  40                  45

Lys Leu Leu Val Ser Tyr Ala Ser Thr Arg His Thr Gly Val Pro Asp
    50                  55                  60

Arg Phe Val Gly Ser Gly Ser Gly Thr Asp Phe Ile Leu Thr Ile Tyr
65                  70                  75                  80

Asn Phe Gln Thr Glu Asp Leu Gly Asp Tyr Tyr Cys Gln Gln His Tyr
                85                  90                  95

Ser Ser Pro Arg Thr Phe Gly Pro Gly Thr Lys Leu Lys Ile Lys Arg
            100                 105                 110

<210> SEQ ID NO 20
<211> LENGTH: 119
<212> TYPE: PRT
<213> ORGANISM: Cricetulus migratorius

<400> SEQUENCE: 20

Gln Val Gln Leu Gln Gln Ser Gly Ala Glu Leu Val Lys Pro Gly Ala
1               5                   10                  15

Ser Val Arg Leu Ser Cys Lys Thr Ser Gly Tyr Thr Phe Thr Thr His
            20                  25                  30

Tyr Val Ser Trp Val Lys Gln Lys Pro Gly Gln Gly Leu Glu Trp Ile
        35                  40                  45

Gly Trp Ile Phe Gly Gly Ser Ala Arg Thr Asn Tyr Asn Gln Lys Phe
    50                  55                  60

Gln Gly Lys Ala Thr Leu Thr Val Asp Thr Ser Ser Lys Ala Tyr
65                  70                  75                  80

Met Asp Leu Arg Ser Leu Thr Ser Asp Ser Ala Val Tyr Phe Cys
                85                  90                  95

Val Arg Gln Val Gly Trp Asp Asp Ala Leu Asp Phe Trp Gly Gln Gly
            100                 105                 110

Thr Gln Val Thr Val Ser Ser
        115

<210> SEQ ID NO 21
<211> LENGTH: 218
<212> TYPE: PRT
<213> ORGANISM: Artificial
<220> FEATURE:
<223> OTHER INFORMATION: Chimeric Cricetulus migratorius and Human

```
<400> SEQUENCE: 21

Asp Ile Val Met Thr Gln Ser Pro Ser Ser Leu Ala Val Ser Ala Gly
 1               5                  10                  15

Asp Thr Val Thr Ile Asn Cys Arg Ser Ser Gln Ser Leu Phe Ser Gly
                20                  25                  30

Asn Tyr Asn Tyr Leu Ala Trp Tyr Gln Gln Lys Thr Gly Gln Thr Pro
            35                  40                  45

Lys Leu Leu Ile Ser Tyr Ala Ser Thr Arg His Thr Gly Val Pro Asp
    50                  55                  60

Arg Phe Val Gly Ser Gly Ser Gly Thr Asp Phe Ile Leu Thr Ile Tyr
65                  70                  75                  80

Asn Phe Gln Thr Glu Asp Leu Gly Asp Tyr Tyr Cys Gln Gln His Tyr
                85                  90                  95

Ser Ser Pro Arg Thr Phe Gly Pro Gly Thr Lys Leu Lys Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 22
<211> LENGTH: 449
<212> TYPE: PRT
<213> ORGANISM: Artificial
<220> FEATURE:
<223> OTHER INFORMATION: Chimeric Cricetulus migratorius and Human

<400> SEQUENCE: 22

Gln Val Gln Leu Gln Gln Ser Gly Ala Glu Leu Val Lys Pro Gly Ala
 1               5                  10                  15

Ser Val Arg Leu Ser Cys Lys Thr Ser Gly Tyr Thr Phe Thr Thr His
                20                  25                  30

Tyr Val Ser Trp Val Lys Gln Lys Pro Gly Gln Gly Leu Glu Trp Ile
            35                  40                  45

Gly Trp Ile Phe Gly Gly Ser Ala Arg Thr Asn Tyr Asn Gln Lys Phe
    50                  55                  60

Gln Gly Lys Ala Thr Leu Thr Val Asp Thr Ser Ser Ser Thr Ala Tyr
65                  70                  75                  80

Met Asp Leu Arg Ser Leu Thr Ser Asp Ser Ala Val Tyr Phe Cys
                85                  90                  95

Val Arg Gln Val Gly Trp Asp Asp Ala Leu Asp Phe Trp Gly Gln Gly
            100                 105                 110

Thr Gln Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
```

```
                130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 23
<211> LENGTH: 112
<212> TYPE: PRT
<213> ORGANISM: Cricetulus migratorius

<400> SEQUENCE: 23

Asp Ile Val Met Thr Gln Ser Pro Ser Ser Leu Ala Val Ser Ala Gly
1               5                   10                  15

Asp Thr Val Thr Ile Asn Cys Arg Ser Ser Gln Ser Leu Phe Ser Gly
            20                  25                  30

Asn Tyr Asn Tyr Leu Ala Trp Tyr Gln Gln Lys Thr Gly Gln Thr Pro
        35                  40                  45

Lys Leu Leu Ile Ser Tyr Ala Ser Thr Arg His Thr Gly Val Pro Asp
    50                  55                  60
```

-continued

Arg Phe Val Gly Ser Gly Ser Gly Thr Asp Phe Ile Leu Thr Ile Tyr
65                  70                  75                  80

Asn Phe Gln Thr Glu Asp Leu Gly Asp Tyr Tyr Cys Gln Gln His Tyr
            85                  90                  95

Ser Ser Pro Arg Thr Phe Gly Pro Gly Thr Lys Leu Lys Ile Lys Arg
        100                 105                 110

<210> SEQ ID NO 24
<211> LENGTH: 119
<212> TYPE: PRT
<213> ORGANISM: Cricetulus migratorius

<400> SEQUENCE: 24

Gln Val Gln Leu Gln Gln Ser Gly Ala Glu Leu Val Lys Pro Gly Ala
1               5                   10                  15

Ser Val Arg Leu Ser Cys Lys Thr Ser Gly Tyr Thr Phe Thr Thr His
            20                  25                  30

Tyr Val Ser Trp Val Lys Gln Lys Pro Gly Gln Gly Leu Glu Trp Ile
        35                  40                  45

Gly Trp Ile Phe Gly Gly Ser Ala Arg Thr Asn Tyr Asn Gln Lys Phe
    50                  55                  60

Gln Gly Lys Ala Thr Leu Thr Val Asp Thr Ser Ser Ser Thr Ala Tyr
65                  70                  75                  80

Met Asp Leu Arg Ser Leu Thr Ser Asp Ser Ala Val Tyr Phe Cys
                85                  90                  95

Val Arg Gln Val Gly Trp Asp Asp Ala Leu Asp Phe Trp Gly Gln Gly
            100                 105                 110

Thr Gln Val Thr Val Ser Ser
        115

<210> SEQ ID NO 25
<211> LENGTH: 132
<212> TYPE: PRT
<213> ORGANISM: Cricetulus migratorius

<400> SEQUENCE: 25

Met Glu Ser His Asn Glu Val Leu Val Thr Leu Leu Leu Trp Val Ser
1               5                   10                  15

Gly Ala Cys Ala Asp Ile Val Met Thr Gln Ser Pro Ser Ser Leu Ala
            20                  25                  30

Val Ser Ala Gly Asp Thr Val Thr Ile Asn Cys Arg Ser Ser Gln Ser
        35                  40                  45

Leu Phe Ser Gly Asn Tyr Asn Tyr Leu Ala Trp Tyr Gln Gln Lys Thr
    50                  55                  60

Gly Gln Thr Pro Lys Leu Leu Ile Ser Tyr Ala Ser Thr Arg His Thr
65                  70                  75                  80

Gly Val Pro Asp Arg Phe Val Gly Ser Gly Ser Gly Thr Asp Phe Ile
                85                  90                  95

Leu Thr Ile Tyr Asn Phe Gln Thr Glu Asp Leu Gly Asp Tyr Tyr Cys
            100                 105                 110

Gln Gln His Tyr Ser Ser Pro Arg Thr Phe Gly Pro Gly Thr Lys Leu
        115                 120                 125

Lys Ile Lys Arg
    130

<210> SEQ ID NO 26
<211> LENGTH: 138

-continued

```
<212> TYPE: PRT
<213> ORGANISM: Cricetulus migratorius

<400> SEQUENCE: 26

Met Gly Trp Ser Trp Ile Ile Leu Phe Leu Val Thr Ala Ala Thr Gly
1               5                   10                  15

Val His Ser Gln Val Gln Leu Gln Gln Ser Gly Ala Glu Leu Val Lys
                20                  25                  30

Pro Gly Ala Ser Val Arg Leu Ser Cys Lys Thr Ser Gly Tyr Thr Phe
            35                  40                  45

Thr Thr His Tyr Val Ser Trp Val Lys Gln Lys Pro Gly Gln Gly Leu
        50                  55                  60

Glu Trp Ile Gly Trp Ile Phe Gly Gly Ser Ala Arg Thr Asn Tyr Asn
65                  70                  75                  80

Gln Lys Phe Gln Gly Lys Ala Thr Leu Thr Val Asp Thr Ser Ser Ser
                85                  90                  95

Thr Ala Tyr Met Asp Leu Arg Ser Leu Thr Ser Asp Asp Ser Ala Val
                100                 105                 110

Tyr Phe Cys Val Arg Gln Val Gly Trp Asp Asp Ala Leu Asp Phe Trp
            115                 120                 125

Gly Gln Gly Thr Gln Val Thr Val Ser Ser
        130                 135
```